(12) United States Patent
Richter

(10) Patent No.: US 8,980,833 B2
(45) Date of Patent: Mar. 17, 2015

(54) TUBULYSINE DERIVATIVES

(75) Inventor: Wolfgang Richter, Munich (DE)

(73) Assignee: R&D-Biopharmaceuticals GmbH, Martinsried (DE)

( * ) Notice: Subject to any disclaimer, the term of this patent is extended or adjusted under 35 U.S.C. 154(b) by 1422 days.

(21) Appl. No.: 12/599,663

(22) PCT Filed: May 9, 2008

(86) PCT No.: PCT/EP2008/003762
§ 371 (c)(1),
(2), (4) Date: Jan. 4, 2011

(87) PCT Pub. No.: WO2008/138561
PCT Pub. Date: Nov. 20, 2008

(65) Prior Publication Data
US 2012/0129779 A1    May 24, 2012

Related U.S. Application Data

(60) Provisional application No. 60/928,781, filed on May 10, 2007.

(51) Int. Cl.
*A61K 38/05* (2006.01)
*C07K 5/02* (2006.01)
*C07K 5/078* (2006.01)

(52) U.S. Cl.
CPC ............. *C07K 5/021* (2013.01); *C07K 5/06139* (2013.01)
USPC ........................ 514/16.6; 514/19.2; 514/21.92

(58) Field of Classification Search
None
See application file for complete search history.

(56) References Cited

FOREIGN PATENT DOCUMENTS

| DE | 102 30 874 A1 | | 1/2004 |
|---|---|---|---|
| DE | 102 30 875 A1 | | 1/2004 |
| WO | 2004/005326 A2 | | 1/2004 |
| WO | 2004/005327 A1 | | 1/2004 |
| WO | WO 2004/005327 | * | 1/2004 |
| WO | 2004/046170 A2 | | 6/2004 |
| WO | WO 2004/046170 | * | 6/2004 |

OTHER PUBLICATIONS

Kaur et al. (Biological evaluation of tubulysin A: a potential anticancer and antiangiogenic natural product. Biochem J. Jun. 1, 2006; 396(Pt 2): 235-242. Published online May 15, 2006. Prepublished online Feb. 20, 2006. doi: 10.1042/BJ20051735 PMCID: PMC1462728 (http://www.ncbi.nlm.nih.gov/pmc/articles/PMC1462728/).*

* cited by examiner

*Primary Examiner* — Karlheinz R Skowronek
*Assistant Examiner* — Roy Teller
(74) *Attorney, Agent, or Firm* — Mintz Levin Cohn Ferris Glovsky and Popeo, P.C.; Peter F. Corless

(57) ABSTRACT

The present invention relates to novel cytotoxic molecules and their use for the treatment of cancer and other diseases.

14 Claims, No Drawings

TUBULYSINE DERIVATIVES

The present invention refers to novel cytotoxic molecules and their use for the treatment of cancer and other diseases.

It is an objective of the present invention to provide novel cytotoxic molecules with a highly potent activity against cancer cell lines and tuneable physicochemical properties, in particular solubility as compared to cytotoxic natural products as described e.g. in [WO9813375; A. Dömling, W. Richter, Mol. Diversity. 2005, 9, 141-147]. Moreover, derivatives are provided which are most suitable for targeting and conjugation approaches [Lit.] to enhance the selectivity of the cytotoxic molecules and the therapeutic window of cytotoxic compounds.

The present invention provides a compound of Formula (I):

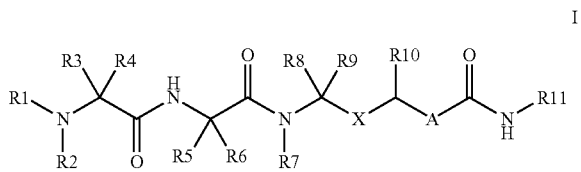

I wherein

A is an optionally substituted 5- or 6-membered heteroaryl ring;

X is O, S or a group of Formula $NR^{12}$, $CR^{13}R^{14}$ or $CH_2CR^{13}R^{14}$;

and $R^1$, $R^2$, $R^3$, $R^4$, $R^5$, $R^6$, $R^7$, $R^8$, $R^9$, $R^{10}$, $R^{12}$, $R^{13}$ and $R^{14}$ are independently of each other H, optionally substituted alkyl, alkenyl, alkinyl, heteroalkyl, especially acetyl or O-acetyl, aryl, heteroaryl, cycloalkyl, alkylcycloalkyl, heteroalkylcycloalkyl, heterocycloalkyl, aralkyl or heteroaralkyl, or two R's together are part of a cycloalkyl or heterocycloalkyl;

$R^{11}$ is a group of the Formula (II)

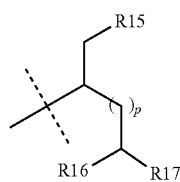

II wherein $R^{15}$ is an optionally substituted aryl, heteroaryl, heterocycloalkyl, heteroalkylcycloalkyl or heteroaralkyl group;

$R^{16}$ is H, an optionally substituted $C_1$-$C_6$ alkyl group, or an optionally substituted aryl or heteroaryl group;

$R^{17}$ is $CO_2H$, $CO_2R^{18}$, $CONHNH_2$, OH, $NH_2$, SH or a branched or unbranched substituted or unsubstituted alkyl, cycloalkyl, heteroalkyl or heterocycloalkyl group, wherein $R^{18}$ is an optionally substituted alkyl, heteroalkyl or heterocycloalkyl group and p is 0, 1, 2 or 3;

or a pharmacologically acceptable salt, a solvate, a hydrate or a pharmacologically acceptable formulation thereof.

Preferably compounds of the following formula (III) are excluded,

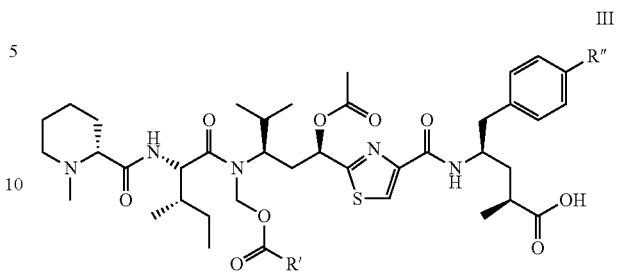

III wherein R' is H, alkyl, alkenyl, aryl, or heteroaryl and R" is H, OH. Especially preferred, the following compounds are excluded: Tubulysins A, B, C, D, E, F, G, H and I.

The term alkyl or alk refers to a saturated, linear or branched, optionally substituted hydrocarbon group, containing from one to twenty carbon atoms, preferably from one to twelve carbon atoms, mostly preferred from one to six carbon atoms, for example methyl, ethyl, propyl, isopropyl, isobutyl, n-butyl, sek-butyl, tert-butyl, n-pentyl, 2,2-dimethylpropyl, 2-methylbutyl, n-hexyl, 2,2-dimethylbutyl or 2,3-dimethylbutyl.

The term alkenyl and alkinyl refers to an at least partially unsaturated, linear or branched, optionally substituted hydrocarbon group, containing from two to twenty carbon atoms, preferably from two to twelve carbon atoms, mostly preferred from two to six carbon atoms, for example ethenyl, allyl, acetylenyl, propargyl, isoprenyl, or hex-2-enyl. Preferentially, alkenyl groups contain one or two, most preferred one double bond and alkinyl groups contain one or two, most preferred one triple bond.

Optionally the terms alkyl, alkenyl and/or alkinyl refer to groups where one or several, preferentially one, two or three hydrogen atoms are replaced by a halogen atom, preferentially fluorine or chlorine or a 2,2,2-trichlorethyl, or a trifluoromethyl group.

The term heteroalkyl refers to an alkyl, alkenyl or alkinyl group, where one or more, preferentially one, two or three carbon atoms are replaced by an O, N, P, B, Se, Si, or S atom, preferentially O, S or N. The term heteroalkyl also refers to a carboxylic acid or a group derived thereof, for example acyl (alkyl-CO), acylalkyl, alkoxycarbonyl, acyloxy, acyloxyalkyl, carboxyalkylamid or alkoxycarbonyloxy.

Examples of heteroalkyl groups are groups of the formula $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ refers to a H, a $C_1$-$C_6$-alkyl, a $C_2$-$C_6$-alkenyl or a $C_2$-$C_6$-alkinyl group; wherein $R^b$ refers to a H, a $C_1$-$C_6$-alkyl, a $C_2$-$C_6$-alkenyl or a $C_2$-$C_6$-alkinyl group; wherein $R^c$ refers to a H, a $C_1$-$C_6$-alkyl, a $C_2$-$C_6$-alkenyl or a $C_2$-$C_6$-alkinyl group; wherein $R^d$ refers to a H, a $C_1$-$C_6$-alkyl, a $C_2$-$C_6$-alkenyl or a $C_2$-$C_6$-alkinyl group and $Y^a$ refers to a direct binding, a $C_1$-$C_6$-alkylen, a $C_2$-$C_6$-alkenylen or a $C_2$-$C_6$-alkinylen group, wherein each heteroalkyl group can be replace by a carbon atom and one or several hydrogen atoms can be replaced by fluorine or chlorine atoms. Examples of heteroalkyl groups are methoxy, trifluormethoxy, ethoxy, n-propyloxy, iso-propyloxy, tert-butyloxy, methoxymethyl, ethoxymethyl, methoxyethyl, methylamino, ethylamino, dimethylamino, diethylamino, iso-propylethylamino, methyl-aminomethyl, ethylaminomethyl, di-iso-propylaminoethyl, enolether, dimethylaminomethyl, dimethylaminoethyl, acetyl, propionyl, butyryloxy, acetyloxy, methoxycarbonyl, ethoxy-carbonyl, N-ethyl-N-methylcarbamoyl or N-methylcarbamoyl. Other examples of heteroalkyl groups are nitrile, isonitrile, cyanate, thiocyanate, isocyanate, isothiocyanate and alkylnitrile groups.

The term cycloalkyl refers to a saturated or partially unsaturated (e.g. cycloalkenyl) optionally substituted cyclic group, comprising one or several rings, preferentially one or two rings, containing three to fourteen ring carbon atoms, preferentially three to ten, preferentially three, four, five, six or seven ring carbon atoms. Furthermore the term cycloalkyl refers to a group where one or more hydrogen atoms are replaced by F, Cl, Br, I, OH, $=$O, SH, $=$S, NH$_2$, $=$NH, or NO$_2$, or cyclic ketones, for example cyclohexanone, 2-cyclohexenone or cyclopentanone. Examples of cycloalkyl groups are cyclopropyl, cyclobutyl, cyclopentenyl, spiro[4,5]-decanyl, norbornyl, cyclohexyl, cyclopentenyl, cyclohexadienyl, decalinyl, cubanyl, bicyclo[4.3.0]nonyl, tetralin, cyclopentylcyclohexyl, fluorcyclo-hexyl or the cyclohex-2-enyl group.

The term heterocycloalkyl refers to a cycloalkyl as defined above, wherein one or several, preferentially one, two or three ring carbon atoms are replaced by an O, N, Si, Se, P, or S, preferentially O, S or N. Preferentially a heterocycloalkyl group is composed of one or two rings comprising three to ten, preferentially three, four, five, six or seven ring atoms. Moreover the term heterocycloalkyl refers to groups where one or several hydrogen atoms are replaced by F, Cl, Br, I, OH, $=$O, SH, $=$S, NH$_2$ or NO$_2$. Examples of heterocyloalkyl are piperidyl, morpholinyl, urotropinyl, pyrrolidinyl, tetrahydrothiophenyl, tetrahydropyranyl, tetrahydro-furyl, oxacyclopropyl, azacyclopropyl or 2-pyrazolinyl groups as well as lactams, lactons, cyclic imides and cyclic anhydrides.

The term alkylcycloalkyl refers to groups, which contain cycloalkyl as well as alkyl, alkenyl or alkinyl groups according to the above definition, e.g. alkylcycloalkyl, alkylcycloalkenyl, alkenylcycloalkyl and alkinylcycloalkyl groups. Preferentially an alkylcycloalkyl group is composed of a cycloalkyl group, comprising one or more rings, comprising three to ten, preferentially three, four, five, six or seven carbon atoms and one or two alkyl, alkenyl oder alkinyl groups with one or two to six carbon atoms.

The term heteroalkylcycloalkyl refers to alkylcycloalkyl groups, according to the above definition, wherein one or several, preferentially one, two or three carbon atoms are replaced by O, N, Si, Se, P or S, preferentially O, S or N. Preferentially it is composed of one or two ring systems with three to ten, preferentially three, four, five, six or seven ring atoms and one or two alkyl, alkenyl, alkinyl or heteroalkyl groups with one or two to six carbon atoms. Examples of such a group are alkylheterocycloalkyl, alkylheterocycloalkenyl, alkenylheterocycloalkyl, alkinylheterocycloalkyl, heteroalkylcycloalkyl, heteroalkylheterocycloalkyl and heteroalkylheterocylcloalkenyl, wherein the cyclic group is saturated or partially (simply, twofold or threefold) unsaturated.

The term aryl or ar refers to an optionally substituted aromatic group, composed of one or several rings, comprising six to fourteen carbon atoms, preferentially six to ten, preferentially six carbon atoms. The term aryl or ar can also refer to an aromatic group, wherein one or several H atoms are replaced by F, Cl, Br or I or OH, SH, NH$_2$, or NO$_2$. Examples are phenyl-, naphthyl-, biphenyl-, 2-fluorphenyl, anilinyl-, 3-nitrophenyl or 4-hydroxy-phenyl.

The term heteroaryl refers to an aromatic group, composed of one or several rings, comprising five to fourteen ring atoms, preferentially five to ten, whereof one or several, preferentially one, two, three or four are O, N, P or S ring atoms, preferentially O, S or N. The term heteroaryl can also refer to groups, wherein one or several H atoms are replaced by F, Cl, Br or I or OH, SH, NH$_2$, or NO$_2$. Examples are 4-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, chinolinyl, purinyl, carbazolyl, acridinyl, pyrimidyl, 2,3'-bifuryl, 3-pyrazolyl and isochinolinyl.

The term aralkyl refers to groups composed of aryl and alkyl, alkenyl, alkinyl and/or cycloalkyl, e.g. arylalkyl, arylalkenyl, arylalkinyl, arylcycloalkyl, arylcycloalkenyl, alkylarylacycloalkyl and alkylarylcycloalkenyl. Examples of aralkyles are toluol, xylol, mesitylen, styren, benzylchloride, o-fluortoluene, 1H-inden, tetralin, dihydronaphthaline, indanon, phenylcyclopentyl, cumol, cyclo-hexylphenyl, fluoren and indan. Preferentially, an aralkyl group is composed of one or two aromatic rings, comprising six to ten ring carbon atoms and one or two alkyl, alkenyl and/or alkinyl comprising one or two to six carbon atoms and/or one cycloalkyl comprising five or six ring carbon atoms.

The term heteroaralkyl refers to an aralkyl group as defined above, wherein one or several, preferentially one, two, three or four carbon atoms are replaced by O, N, Si, Se, P, B or S, preferentially O, N or S, and to groups which contain aryl, heteroaryl and alkyl, alkenyl, alkinyl and/or heteroalkyl and/or cycloalkyl and/or heterocycloalkyl. Preferentially a heteroaralkyl group is composed of one or two aromatic ring systems comprising five or six to ten carbon atoms and one or two alkyl, alkenyl and/or alkinyl comprising one or two to six carbon atoms and/or one cycloalkyl comprising five or six ring carbon atoms, wherein one, two, three or four carbon atoms can be replaced by O, N or S.

Examples are arylheteroalkyl, arylheterocycloalkyl, arylheterocycloalkenyl, arylalkylheterocycloalkyl, arylalkenylheterocycloalkyl, arylalkinylheterocyclo-alkyl, arylalkylheterocycloalkenyl, heteroarylalkyl, heteroarylalkenyl, heteroarylalkinyl, heteroarylheteroalkyl, heteroarylcycloalkyl, heteroarylcycloalkenyl, heteroarylheterocycloalkyl, heteroarylheterocycloalken-yl, heteroarylalkylcycloalkyl, heteroarylalkylhetero-cycloalkenyl, heteroarylheteroalkylcycloalkyl, heteroarylheteroalkylcycloalkenyl and heteroarylheteroalkyl heterocycloalkyl, wherein the cyclic groups can be saturated or once, twice, three fold of four fold unsaturated. Examples are tetrahydroiso-chinolinyl, benzoyl, 2- or 3-ethyl-indolyl, 4-methylpyridino, 2-, 3- or 4-methoxyphenyl, 4-ethoxyphenyl, 2-, 3- or 4-carboxyphenylalkyl.

The terms cycloalkyl, heterocycloalkyl, alkylcyclo-alkyl, heteroalkylcycloalkyl, aryl, heteroaryl, aralkyl and heteroaralkyl also refer to groups, wherein one or several H atoms are replaced by F, Cl, Br or I or OH, SH, NH$_2$, NO$_2$.

The term "optionally substituted" relates to groups, wherein one or several H atoms can be replaced by F, Cl, Br or I or OH, SH, NH$_2$, or NO$_2$. This term relates further to groups, which can be exclusively or additionally substituted with unsubstituted $C_1$-$C_6$ alkyl, $C_2$-$C_6$ alkenyl, $C_2$-$C_6$ alkinyl, $C_1$-$C_6$ heteroalkyl, $C_3$-$C_{10}$ cycloalkyl, $C_2$-$C_9$ heterocycloalkyl, $C_6$-$C_{10}$ aryl, $C_1$-$C_9$ heteroaryl, $C_7$-$C_{12}$ aralkyl or $C_2$-$C_{11}$ heteroaralkyl.

Protecting groups are known to a person skilled in the art and described in P. J. Kocienski, Protecting Groups, Georg Thieme Verlag, Stuttgart, 1994 and in T. W. Greene, P. G. M. Wuts, Protective Groups in Organic Synthesis, John Wiley & Sons, New York, 1999. Common amino protecting groups are e.g. t-butyloxycarbonyl (Boc), benzyloxycarbonyl (Cbz, Z), benzyl (Bn), benzoyl (Bz), fluorenylmethyloxycarbonyl (Fmoc), allyloxycarbonyl (Alloc), trichlorethyloxycarbonyl (Troc), acetyl or trifluoracetyl.

Compounds of Formula (I) and (II) can comprise several chiral centers depending on their substitution pattern. The present invention relates to all defined enantio and diastereo isomers as well as their mixtures in all ratios. Moreover the present invention relates to all cis/trans isomers of compounds of the general Formula (I) and (II) as well as their mixtures. Moreover the present invention relates to all tautomeric forms of compounds of the general Formula (I) and (II).

Preferably A has the following structure:

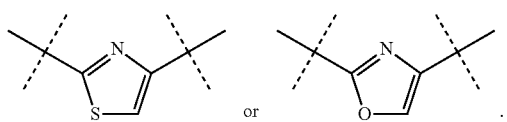

Moreover preferably X is a CH$_2$ group.
Preferably R$^2$ is a C$_1$-C$_4$ alkyl.
Preferably R$^1$ and R$^3$ are together (CH$_2$)$_n$ with n=2, 3, 4 or 5, preferably 3 or 4.
Preferably R$^4$ is H or methyl, especially H.
Preferably R$^5$ is H.
Preferably R$^6$ is optionally branched C$_1$-C$_6$ alkyl, C$_3$-C$_6$ cycloalkyl or C$_4$-C$_7$ alkyl cycloalkyl, especially isobutyl.
Preferably R$^7$ is optionally branched alkyl like methyl, ethyl, propyl, isopropyl, n-butyl, isobutyl, CH$_2$OR$^{19}$, C(O)R$^{19}$ or CH$_2$OCOR$^{20}$, wherein R$^{19}$ is optionally branched alkyl, especially isopropyl, R$^{20}$ is optionally branched C$_1$-C$_6$ alkyl or C$_2$-C$_6$ alkenyl.
Further preferred R$^7$ is an optionally substituted alkyl; —R$^{22}$—O—R$^{23}$, wherein R$^{22}$ is alkylen, especially methylen or ethylen, and R$^{23}$ is an alkyl, alkenyl, cycloalkyl, heterocycloalkyl, aryl, or heteroaryl group; C(O)R$^{19}$, wherein R$^{19}$ is an alkyl group, especially isopropyl; CH$_2$OCOPh; CH$_2$OCOCH$_2$Ph; —R$^{22}$—NR$^{24}$R$^{25}$, wherein R$^{22}$ is alkylen, and R$^{24}$ and R$^{25}$ are independently of each other H or alkyl; or R$^{26}$—OH, wherein R$^{26}$ is an alkyl.
More preferred R$^7$ is a C$_1$-C$_8$-alkyl; —R$^{22}$—O—R$^{23}$, wherein R$^{22}$ is C$_1$-C$_6$-alkylen, especially methylen or ethylen, and R$^{23}$ is a C$_1$-C$_6$-alkyl, C$_2$-C$_6$-alkenyl, cycloalkyl, heterocycloalkyl, aryl, or heteroaryl group; C(O)R$^{19}$, wherein R$^{19}$ is a C$_1$-C$_6$-alkyl group, especially isopropyl; CH$_2$OCOPh; or CH$_2$OCOCH$_2$Ph.
Preferably R$^8$ is optionally branched C$_1$-C$_6$ alkyl, like methyl, ethyl, propyl, isopropyl, n-butyl or isobutyl, especially isopropyl.
Preferably R$^9$ is H or methyl.
Preferably R$^{10}$ is H, OH, —(C═O)—(C$_{1-4}$)alkyl, O-alkyl or O-acetyl.

Preferably R$^{15}$ is aralkyl or heteroaralkyl; especially preferred R$^{15}$ is a group of the Formula

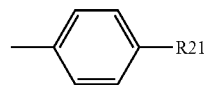

wherein R$^{21}$ is H, halogen, OH, NO$_2$, NH$_2$, CN, alkyl, heteroalkyl, cyclo-alkyl, heterocycloalkyl, aryl, heteroaryl, alkyloxy, alkyl amino or dialkyl amino.
Especially preferred, R$^{21}$ is H, halogen, especially F, OH, OMe, Phe, or NMe$_2$.
Preferably p is 1 or 2.
Most preferable are compounds of Formula (IV),

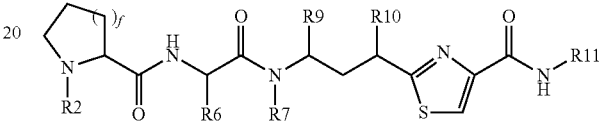

wherein R$^2$ is C$_1$-C$_4$ alkyl, R$^6$ is C$_1$-C$_6$ alkyl, R$^7$ is C$_1$-C$_6$ alkyl, CH$_2$OR$^{19}$ or CH$_2$OCOR$^{20}$, wherein R$^{19}$ is alkyl, especially isopropyl, R$^{20}$ is C$_2$-C$_6$-alkenyl, phenyl, or CH$_2$-Phenyl, R$^9$ is C$_1$-C$_6$ alkyl, R$^{10}$ is H, OH, O-alkyl or O-acetyl and f is 1 or 2.
Preferentially R$^{11}$ has the following structure in formula (I) or (IV):

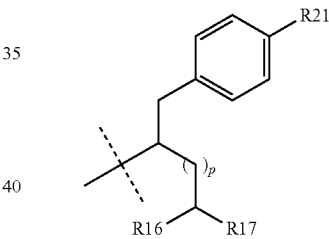

wherein R$^{21}$ is H, OH, halogen, NH$_2$, alkyloxy, phenyl, alkyl amino or dialkyl amino; R$^{16}$ is H or a C$_1$-C$_6$-alkyl group; R$^{17}$ is CO$_2$H, CO$_2$R$^{18}$, CONHNH$_2$, OH, NH$_2$, SH or a optionally substituted alkyl, cycloalkyl, heteroalkyl or heterocycloalkyl group, wherein R$^{18}$ is an optionally substituted alkyl, heteroalkyl or heterocycloalkyl group;
p is 0, 1, 2 or 3.
Especially preferred are compounds of the following formula:

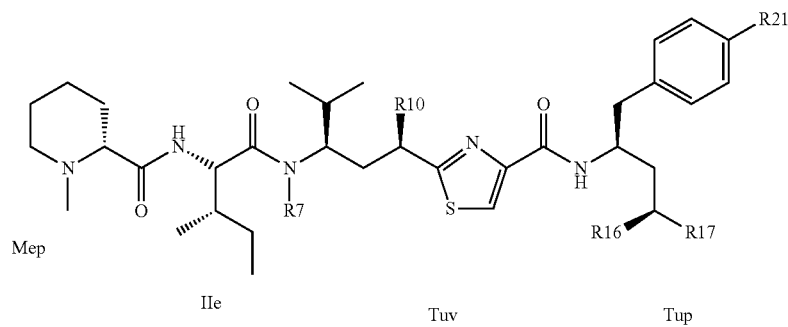

wherein: $R^7$=$C_1$-$C_6$ alkyl, especially $CH_3$, ethyl, propyl, isopropyl, isobutyl, n-pentyl, n-hexyl, $CH_2Ph$, $CH_2OCH_2CH(CH_3)_2$, $CH_2OCOCH_2Ph$, or $CH_2OCOPh$ $R^{10}$=H, OH, OAc $R^{16}$=$CH_3$, H $R^{17}$=COOH, $CONHNH_2$, OH, $NH_2$, $CH_2OH$, $CH_2NH_2$, $CH_2SH$ $R^{21}$=H, F, OH, $CH_3$, OMe, Ph Examples of pharmacologically acceptable salts of compounds of Formula (I) or (IV) are physiologically acceptable mineral acids, e.g. hydrochloric acid, sulfuric acid, phorphoric acid or salts of organic acids, e.g. methansulfonic acid, p-toluenesulfonic acid, lactic acid, formic acid, trifluoracetic acid, citric acid, succinic acid, fumaric acid, maleic acid and salicylic acid. Compounds of Formula (I) or (IV) can be solvated, especially hydrated. The hydration can occur during the synthesis process or can be a consequence of the hygroscopic nature of the originally dehydrated compound of Formula (I) or (IV). Compounds of Formula (I) or (IV), containing asymmetric carbon atoms might exist as mixtures of diastereomers, as mixtures of enantiomers or as optically pure compounds.

The pharmaceutical composition according to the present invention is composed of at least one compound of Formula (I) or (IV) and optionally carriers and/or adjuvants.

Prodrugs are also subject of the present invention and they are composed of a compound of Formula (I) or (IV) and at least one pharmacologically acceptable protecting group, which is cleaved under physiological conditions, e.g. alkoxy, aralkyloxy, acyl or acyloxy, more precisely ethoxy, benzyloxy, acetyl or acetyloxy.

Moreover, the present invention relates to conjugates comprising at least one compound of Formula (I) or (IV) and a biological molecule, e.g. oligo and poly saccharides, monoclonale antibody, lectine, PSA (prostata specific antigen) or peptidic vectors, hormones (somatostatin), vitamins (e.g. folic acid and its analogs), lipids or a synthetic polymer and if needed also a suitable linker, respectively. The expression linker relates to a chemical group, which links compounds of Formula (I) or (IV) with such a biological macro-molecule. Examples of linkers are alkyl, heteroalkyl, aryl, heteroaryl, cycloalkyl, heterocycloalkyl, aralkyl or heteroaralkyl linkers.

The therapeutic use of compounds of Formula (I) or (IV), their pharmacologic acceptable salts and/or solvates and hydrates, as well as the corresponding formulations and pharmacological compositions are also subject of the present invention.

The use of the active agents for the preparation of drugs for the treatment of cancer is also subject of the present invention. Moreover, the present compounds are of interest for the prevention and/or treatment of rheumatoid arthritis, inflammatory diseases, immunological diseases (e.g. type I diabetis), autoimmune diseases, diseases of the eye, e.g. AMD (age related macular disease) or diabetic retinopathy other tumor diseases as well as for the surface treatment (impregnation) of plastic and metal implants, e.g. stents. In general, compounds of Formula (I) or (IV) can be given as a single treatment or as multiple treatments either alone or in combination with an arbitrary therapeutic substance according to known and accepted modes or as a continuous treatment whereby the active principle can be embedded in a matrix such as e.g. an implantable hydrogel. Compositions according to the invention can be administered in one of the following ways: orally, including dragees, coated tablets, pills, semi-solids, soft or hard capsules, solutions, emulsions or suspensions; parenteral, including injectable solutions; rectal as suppositories; by inhalation, including powder formulation or as a spray, transdermal or intranasal. For the production of such tablets, pills, semi solids, coated tabletts, dragees and hard gelatine capsules the therapeutically used product is mixed with pharmacologically inert, anorganic or organic carriers, e.g. with lactose, sucrose, glucose, gelatine, malt, silica gel, starch, or derivatives thereof, talkum, stearinic acid or its salts, dried skim milk and the like. For the production of soft capsules one may use carriers like vegetable oils, petroleum, animal or synthetic oils, wax, fat, polyols. For the production of liquid solutions and syrups one may use carriers for example water, alcohols, aqueous saline, aqueous dextrose, polyole, glycerin, vegatable oils, petroleum, animal or synthetic oils. For the production of suppositories one may use excipients like e.g. vegetable, petroleum, animal or synthetic oils, wax, fat and polyols. For aerosol formulations one may use compressed gases suitable fort his purpose like e.g. oxygen, nitrogen, noble gas and carbon dioxide. The pharmaceutically useful agents may also contain additives for conservation, stabilisation, e.g. UV stabilizer, emulsifier, sweetener, aromatiser, salts to change the osmotic pressure, buffers, coating additives and antioxidants.

Combinations with other therapeutic agents can include further agents, which are commonly used to treat the diseases mentioned above, especially cancer.

Compounds of Formula (V), (VI) and (VII) optionally provided with suitable protecting groups are produced as building blocks for the production of compounds of Formula (I) and (IV). These can be linked via peptide coupling methods using known coupling reagents, e.g. hydroxybenzotriazole (HOBt) and diisopropylcarbodiimide (DIC) or dicyclohexylcarbodiimide (DCC). Unless otherwise defined, all residues are defined as herein above.

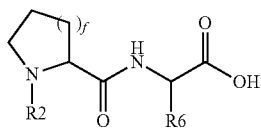

(V)

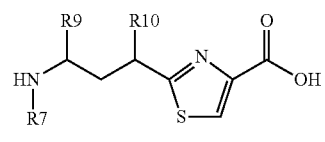

(VI)

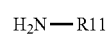

$H_2N-R11$ (VII)

Building block (V) can be produced through peptide coupling of commercially available and known aminoacids.

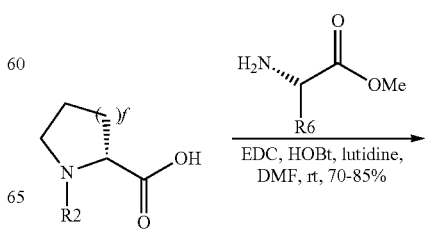

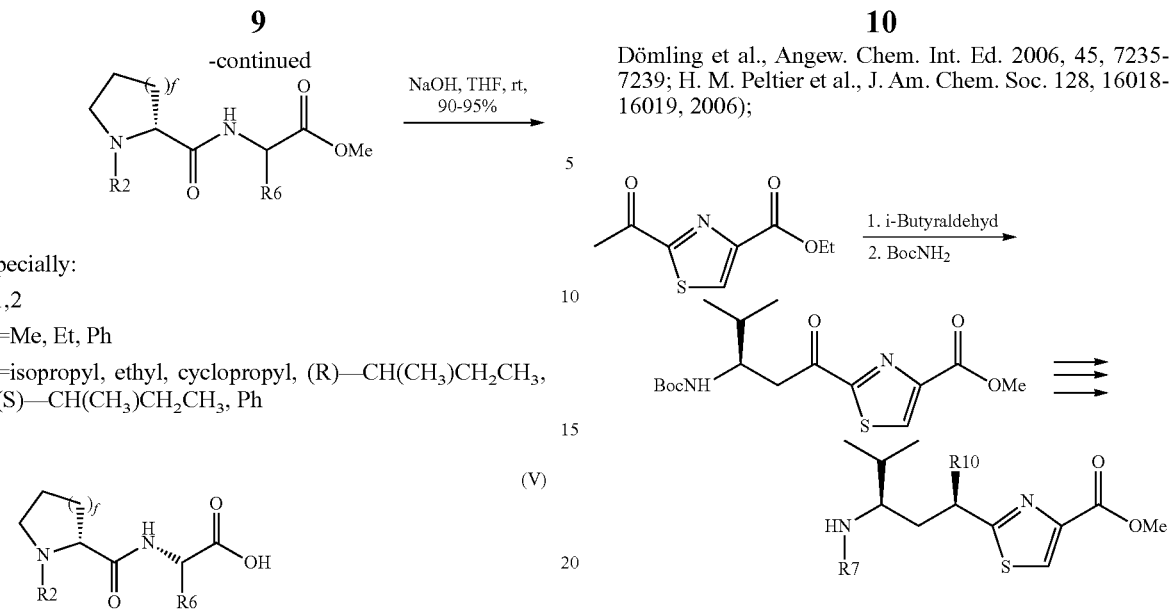

Especially:

f=1,2

R² = Me, Et, Ph

R⁶ = isopropyl, ethyl, cyclopropyl, (R)—CH(CH₃)CH₂CH₃, (S)—CH(CH₃)CH₂CH₃, Ph

The compounds of formulae (VI) and (VII) can be prepared in a manner, known to a person skilled in the art, c.f. for example also described in part in the Lit. (D. Neri, G. Fossati, M. Zanda, ChemMedChem 2006, 1, 175-180; A. Dömling et al., Angew. Chem. Int. Ed. 2006, 45, 7235-7239; H. M. Peltier et al., J. Am. Chem. Soc. 128, 16018-16019, 2006);

Especially:

R⁷ = CH₃, ethyl, propyl, isopropyl, n-pentyl, n-hexyl, CH₂OCOCH₂CH(CH₃)₂, CH₂OCOCH₂CH₃, CH₂OCOCH₂CH₂CH₃, CH₂Ph, CH₂OCH₂CH(CH₃)₂, CH₂OCOCH₂Ph, or CH₂OCOPh R¹⁰ = H, OH, OAc

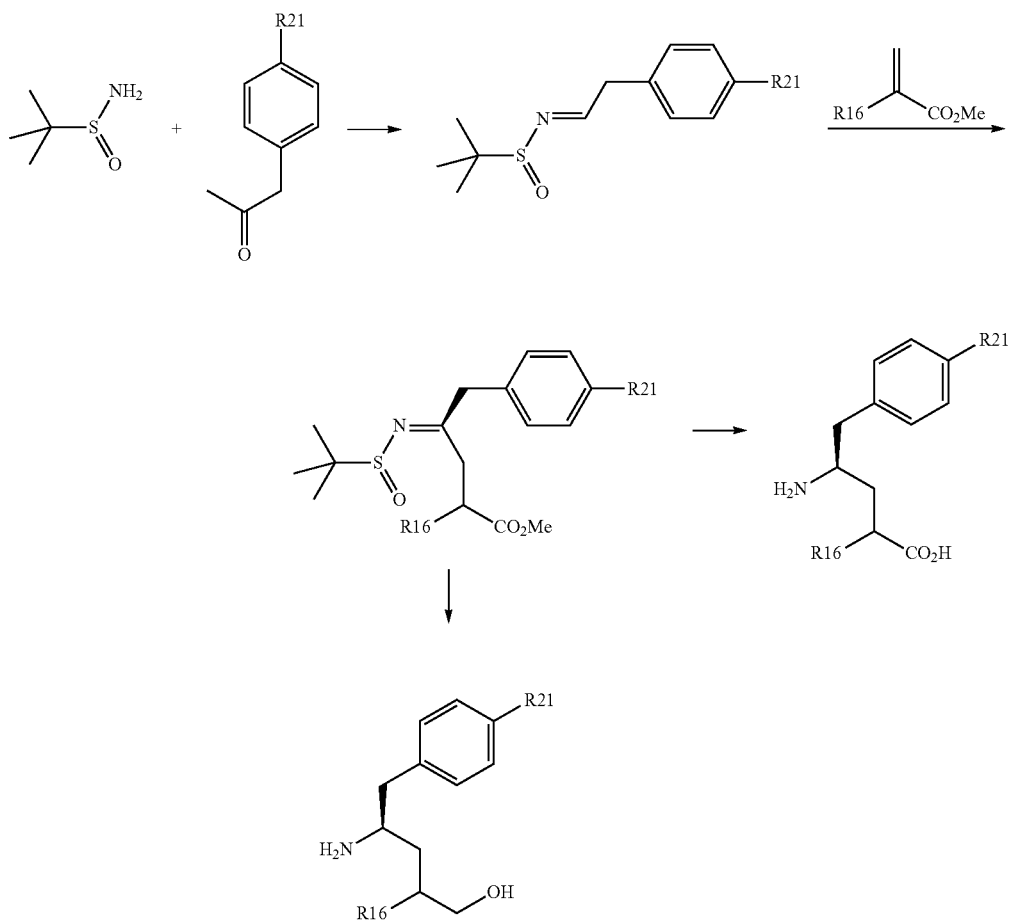

Especially:
R¹⁶=CH₃, H, Ph
R²¹=H, F, OH, OMe, Ph, Cyclohexyl
Especially, the following building blocks can be used for the preparation of compounds according to the present invention.

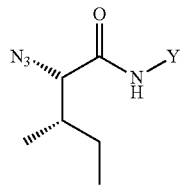

Y is defined as R⁷ above.

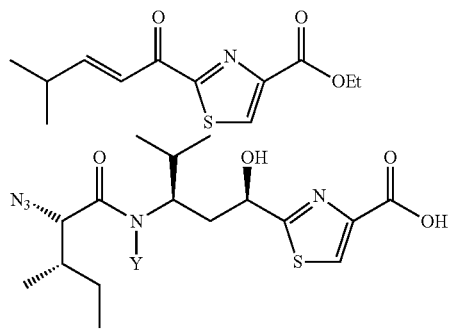

Y is defined as R⁷ above.

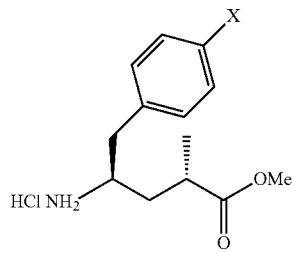

X is defined as R²¹ above.

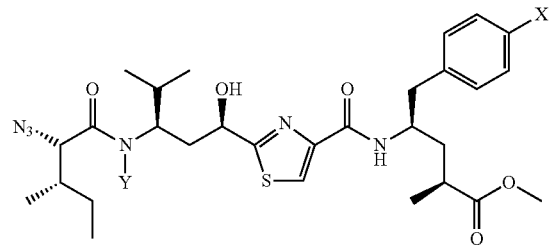

X is defined as R²¹ above.
Y is defined as R⁷ above.

EXAMPLES

According to the herein disclosed synthetic procedures of the building blocks the following derivatives were synthesized according to the usual peptide coupling methods known to a person skilled in the art:

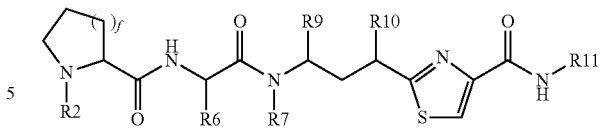

The following residues where used:
f=1, 2;
R²=methyl, ethyl;
R⁶=isopropyl, ethyl, cyclopropyl, (R)—CH(CH₃)CH₂CH₃, (S)—CH(CH₃)CH₂CH₃;
R⁷=methyl, ethyl, propyl, isobutyl, CH₂OCOPh;
R⁹=isopropyl, trifluormethyl, chlormethyl, isobutyl, ethyl, cyclopropyl, CH₂-cyclopropyl, CH(CH₃)CH₂CH₃, cyclopentyl, cyclohexyl;
R¹⁰=H, OH, OAc
R¹¹=

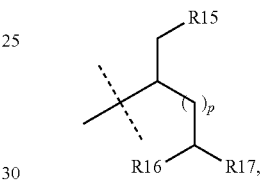

wherein
p=1, 2;

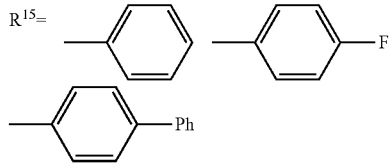

R¹⁶=H, CH3
R¹⁷=COOH, CH₂OH, CH₂NH₂, CONHNH₂, CH₂SH

Representative structures of compounds according to the present invention are presented below:

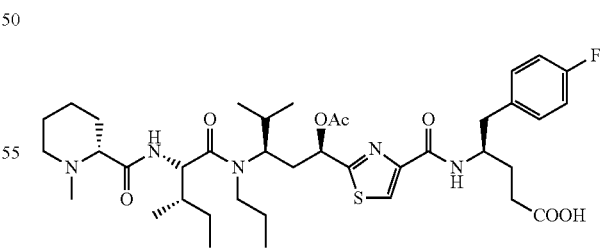

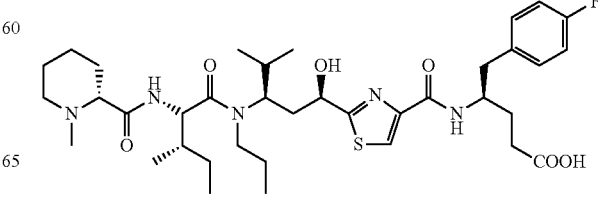

-continued
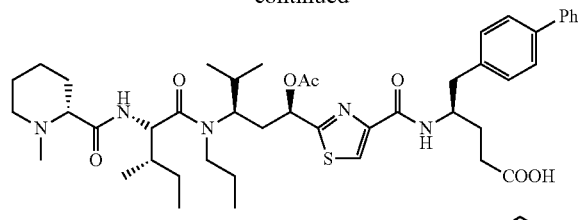
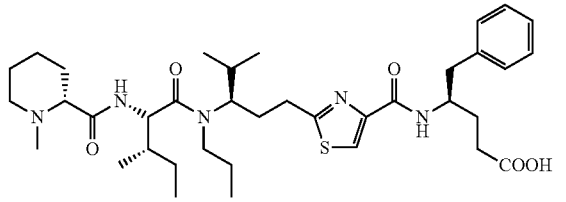
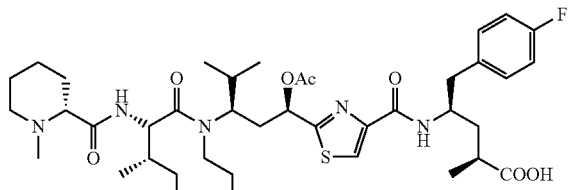
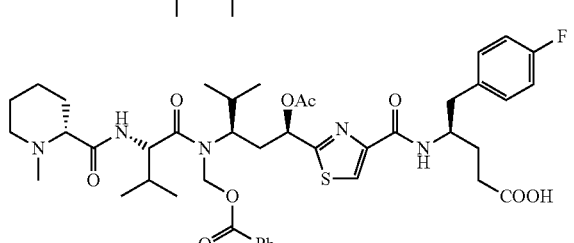
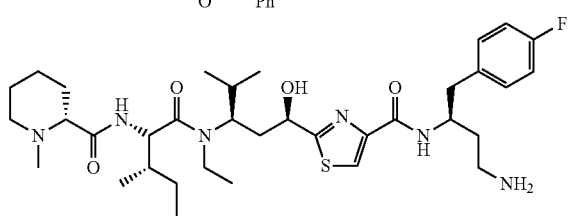
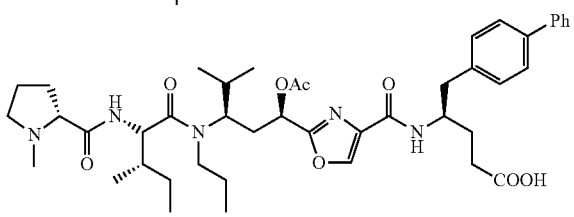
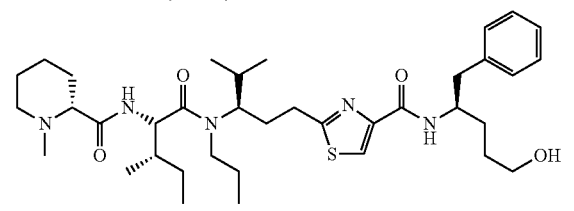
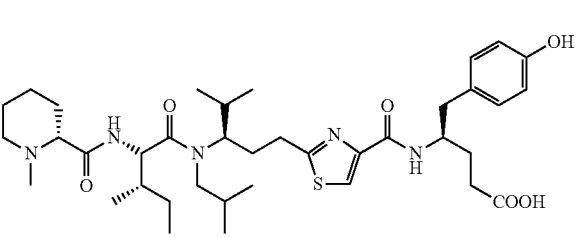
Detailed Synthetic Schemes and Procedures:
1) Mep Precursor and Activation:
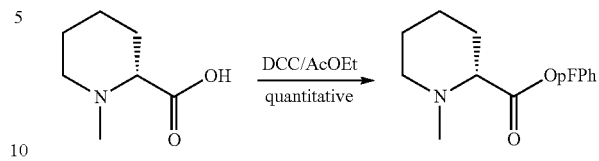
2) Synthesis of Ile-Tuv Part to RD242:
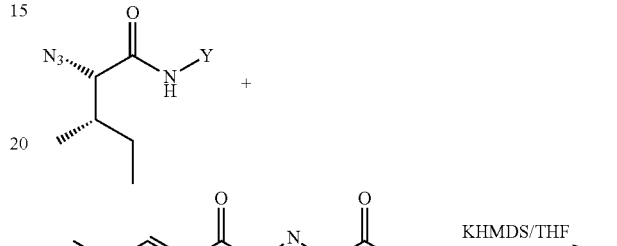
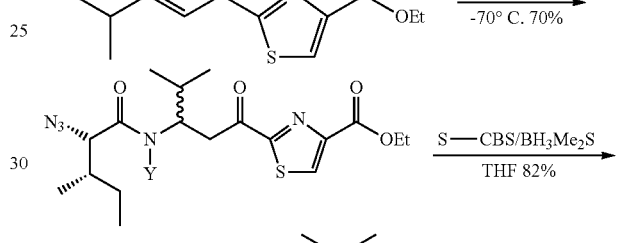
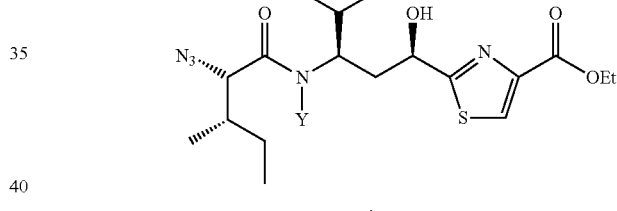
3) Synthesis of the X-Tup Part RD119:
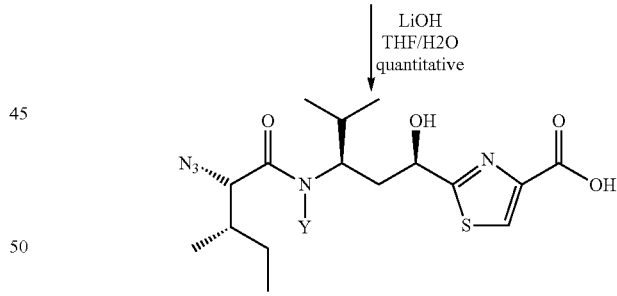

15
-continued
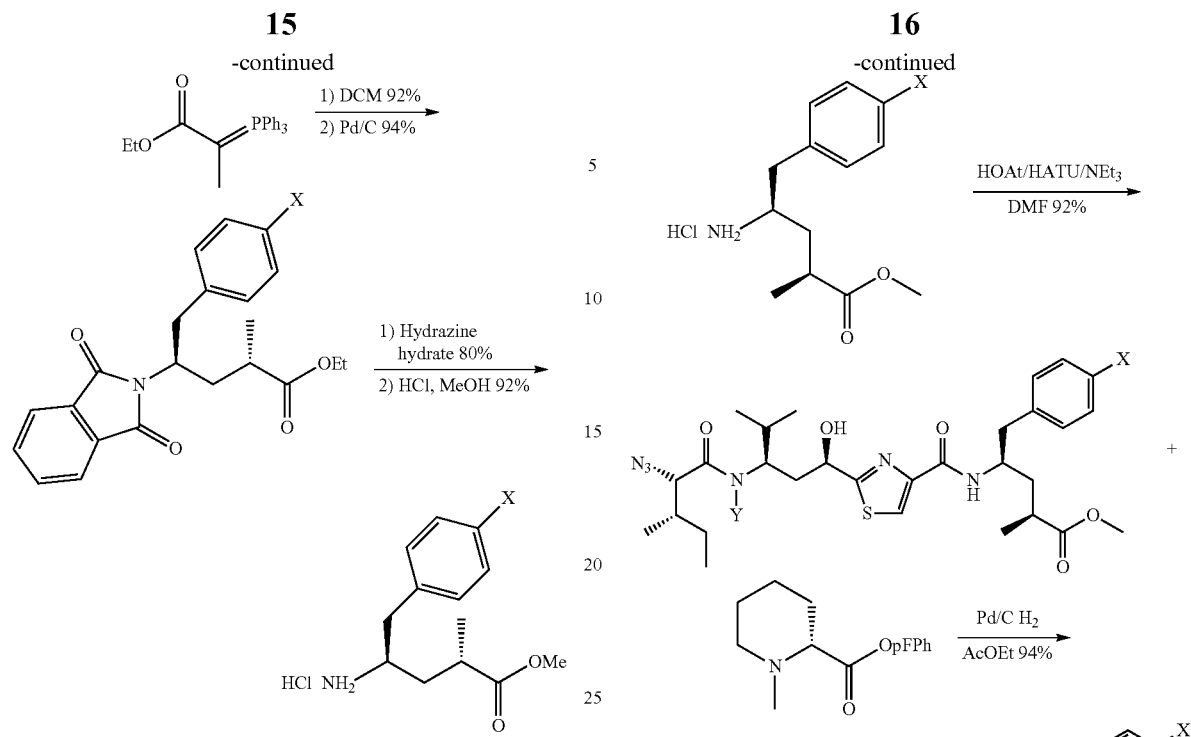
16
-continued
4) Assembly of Building Blocks Azido-Ile-(N-Y)-Tuv (COOH), X-Tup and Activated Mep:
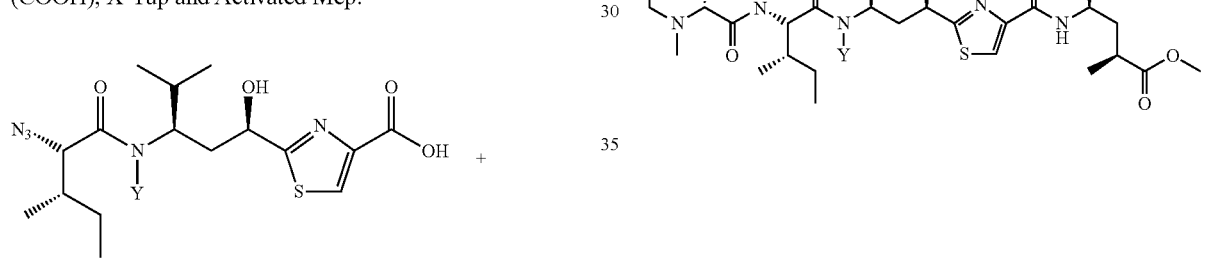
5) Synthesis of Target Molecules:
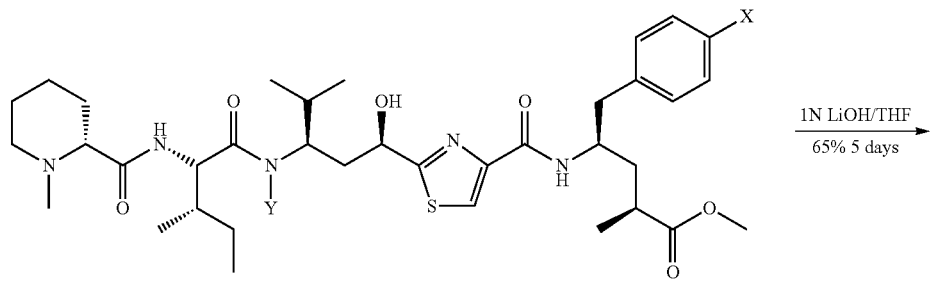
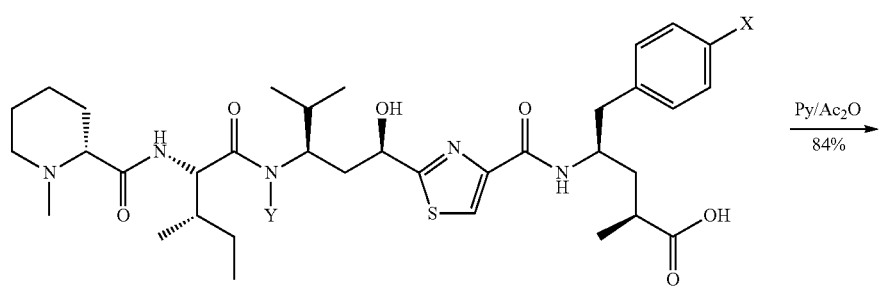

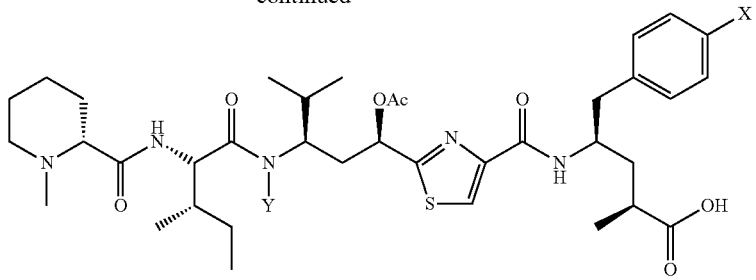

Synthesis of p-FluoroTubuphenylalanine (FTup)

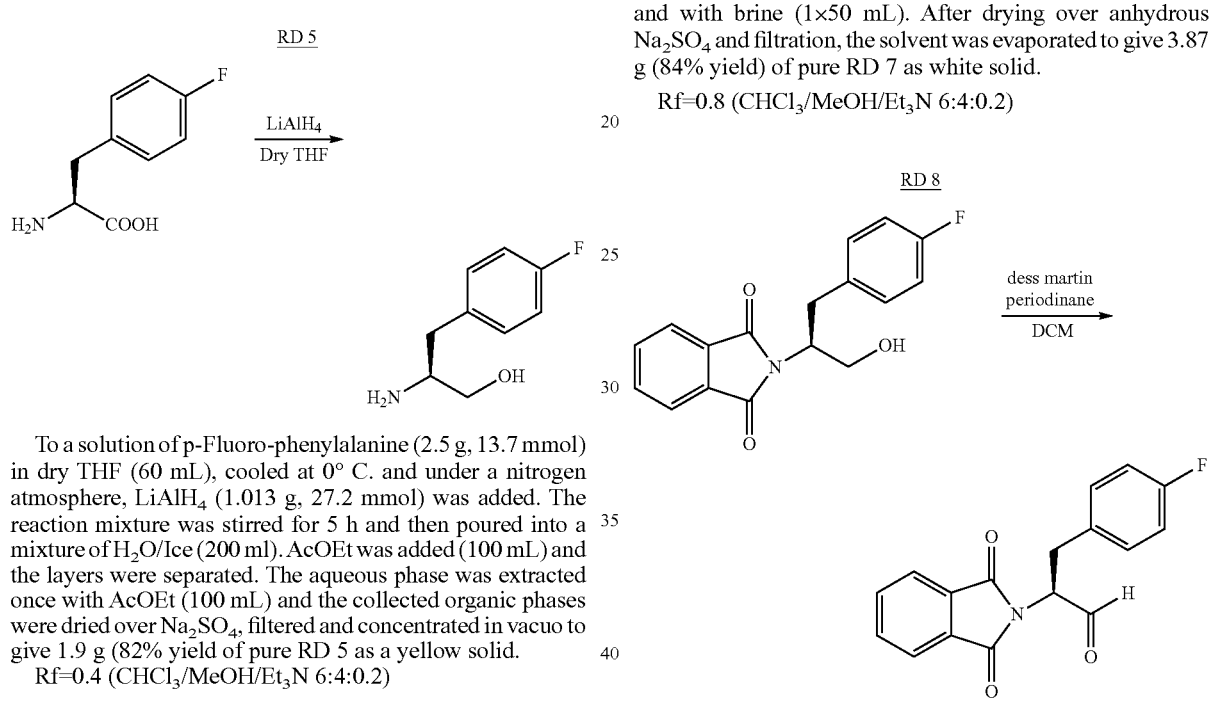

To a solution of p-Fluoro-phenylalanine (2.5 g, 13.7 mmol) in dry THF (60 mL), cooled at 0° C. and under a nitrogen atmosphere, LiAlH$_4$ (1.013 g, 27.2 mmol) was added. The reaction mixture was stirred for 5 h and then poured into a mixture of H$_2$O/Ice (200 ml). AcOEt was added (100 mL) and the layers were separated. The aqueous phase was extracted once with AcOEt (100 mL) and the collected organic phases were dried over Na$_2$SO$_4$, filtered and concentrated in vacuo to give 1.9 g (82% yield of pure RD 5 as a yellow solid.

Rf=0.4 (CHCl$_3$/MeOH/Et$_3$N 6:4:0.2)

To a suspension of F-Phenylalaminol (2.6 g, 15.3 mmol) in toluene (6 mL) phthalic anhydride (2.2 g, 15.3 mmol) and Et$_3$N (200 μL, 1.53 mmol) were added. The reaction flask was equipped with a Dean-Stark apparatus and the reaction was refluxed at 140° C. for 8 h. The solvent was removed in vacuo and the residue was dissolved with AcOEt (100 mL). The organic phase was washed with a 1N aqueous solution of HCl (1×50 mL), a 5% aqueous solution of NaHCO$_3$ (1×50 mL) and with brine (1×50 mL). After drying over anhydrous Na$_2$SO$_4$ and filtration, the solvent was evaporated to give 3.87 g (84% yield) of pure RD 7 as white solid.

Rf=0.8 (CHCl$_3$/MeOH/Et$_3$N 6:4:0.2)

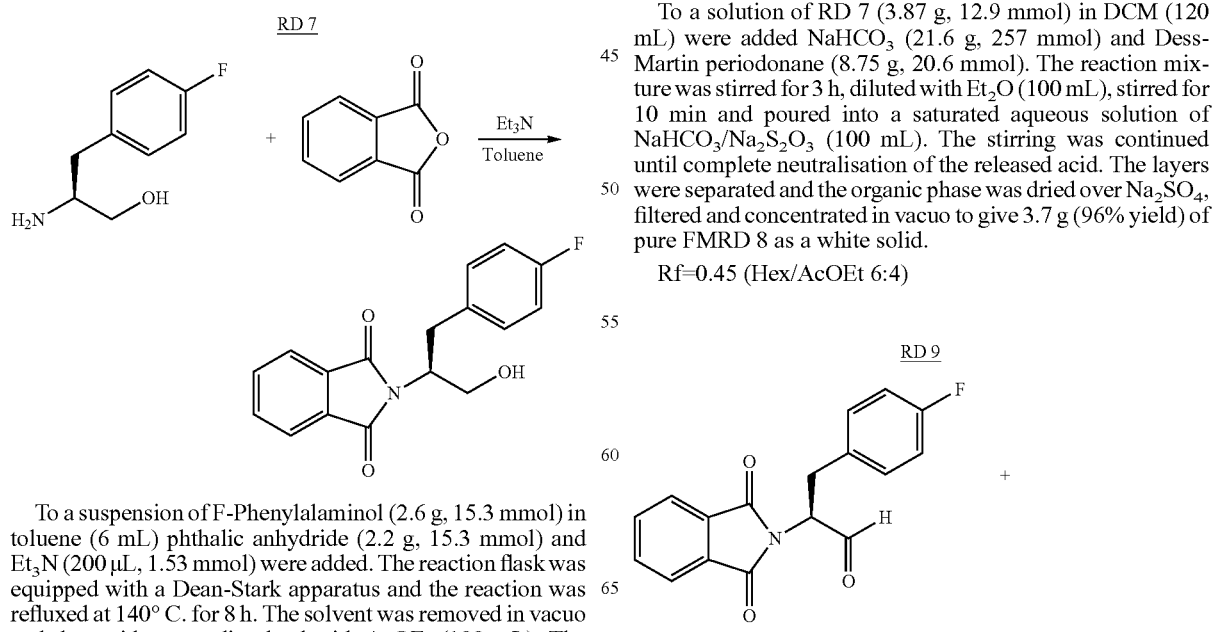

To a solution of RD 7 (3.87 g, 12.9 mmol) in DCM (120 mL) were added NaHCO$_3$ (21.6 g, 257 mmol) and Dess-Martin periodonane (8.75 g, 20.6 mmol). The reaction mixture was stirred for 3 h, diluted with Et$_2$O (100 mL), stirred for 10 min and poured into a saturated aqueous solution of NaHCO$_3$/Na$_2$S$_2$O$_3$ (100 mL). The stirring was continued until complete neutralisation of the released acid. The layers were separated and the organic phase was dried over Na$_2$SO$_4$, filtered and concentrated in vacuo to give 3.7 g (96% yield) of pure FMRD 8 as a white solid.

Rf=0.45 (Hex/AcOEt 6:4)

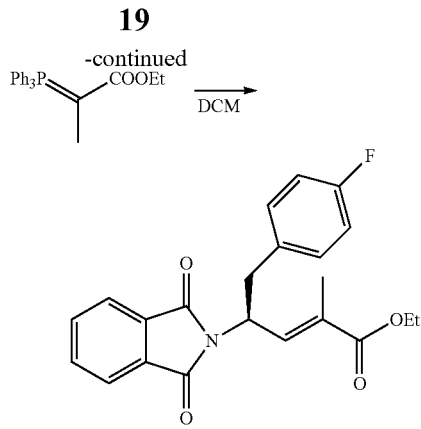

To a solution of 1-ethoxy carbonylethylidene triphenylphosphorane (5.9 g, 16.3 mmol) in DCM (100 mL), cooled at 5° C., N-phthaloyl aldehyde FMRD8 (3.95 g, 13.3 mmol) dissolved in DCM (40 mL) was added dropwise over a period of 30 min. The reaction was stirred for additional 10 min at 5° C. and then the temperature was allowed to warm to r.t. The reaction mixture was stirred for 3 h and then quenched with a 1N aqueous solution of NaHSO$_4$ (80 mL). The layers were separated and the organic phase was washed with brine (1×40 mL), dried over Na$_2$SO$_4$, filtered and concentrated in vacuo. The crude was purified by FC (Hex:AcOEt 8:2) to give 4.35 g of RD 9 (92% yield) as a colorless oil.
Rf=0.5 (Hex/AcOEt 6:4)

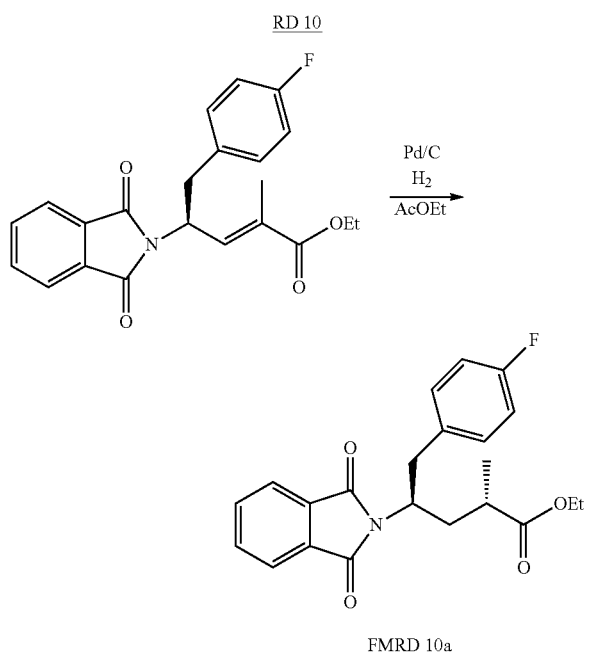

To a solution of RD 9 (4.3 g, 11.3 mmol) in AcOEt (60 mL), a catalytic amount of Pd/C was added. The reaction mixture was stirred under a hydrogen atmosphere overnight and filtered through Celite. The filtrate was concentrated under reduced pressure and the crude was purified by FC (iPrO$_2$:Ex 1:1) to give 2.2 g of RD 10a (Rf>) and 1.9 g of RD 10b (Rf<) as colorless oils (94% overall yield). Rf=0.4 (Hex/iPrO$_2$ 1:1)

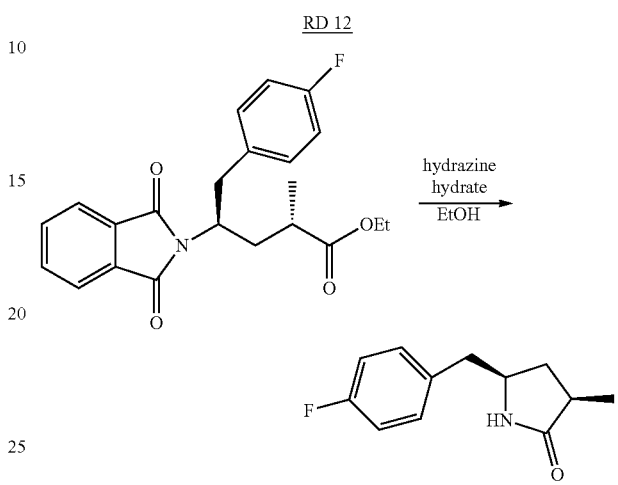

To a solution of RD 10a (2.7 g, 7.0 mmol) in EtOH (70 mL) was added hydrazine hydrate (50% solution w/w in water) (3.4 mL, 35 mmol). The reaction was refluxed for 30 min until a white precipitate was formed and then heated for additional 3 h. The solvent was removed in vacuo and the crude was purified by FC (DCM:MeOH 95:5) to give 1.3 g of RD 12 (92% yield) as a white solid. Rf=0.5 (CHCl$_3$/MeOH 95:5)

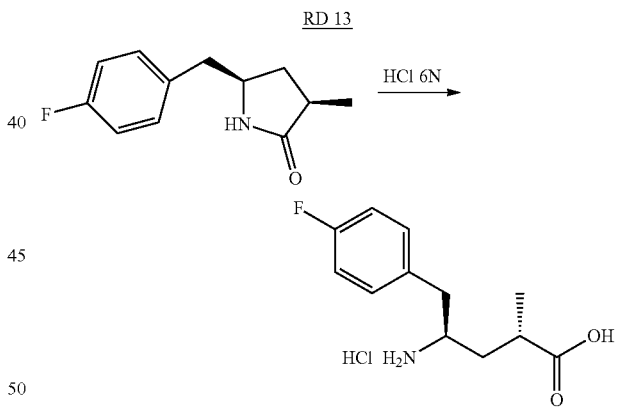

RD 12 (1.3 g, 6.3 mmol) was dissolved in HCl 6N and refluxed for 3 h. The solvent was removed in vacuo to give 1.64 g of pure RD 13 (quantitative yield) as a white solid.

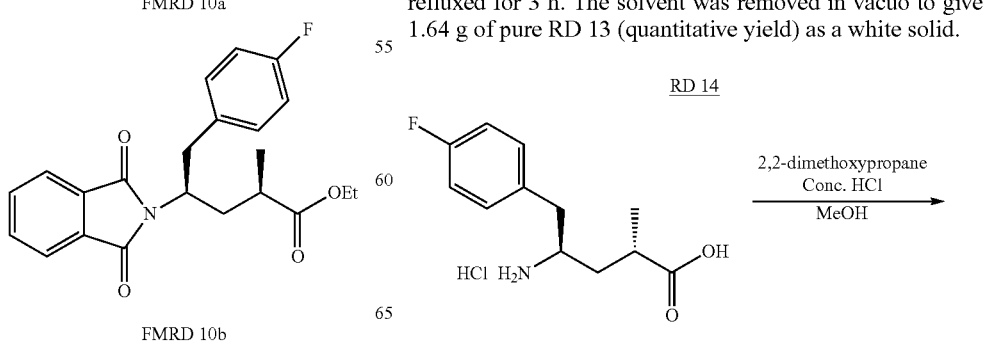

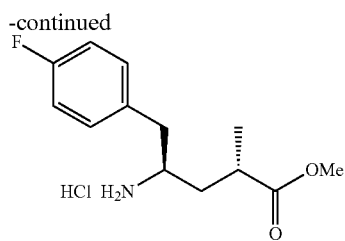

To a solution of RD 13 (1.6 g, 6.1 mmol) in MeOH (30 mL) were added 2,2-dimethoxypropane (1.5 mL, 12.2 mmol) and conc. HCl (18 µL, 0.6 mmol). The reaction mixture was heated at 50° C. overnight. The solvent was removed in vacuo to give 1.35 of pure RD 14 (92% yield) as a white solid.
Rf=0.3 (CHCl$_3$/MeOH 9:1).

Synthesis of N-Me-Tuv Analogue of F-Tubulysin D

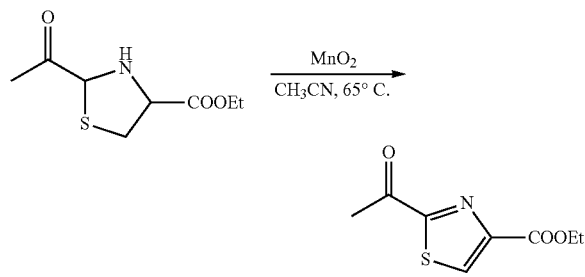

To a solution of Cysteine (30 g, 161.6 mmol) in a 1:1 EtOH/H$_2$O mixture (3 L) were added NaHCO$_3$ (13.6 g, 161.6 mmol) and pyruvic aldehyde (35% w/w in H$_2$O, 40 mL, 228 mmol). The reaction mixture was stirred at r.t for 14 h, then concentrated to half of its original volume at reduced pressure. NaCl was added to saturate the aqueous phase. The aqueous layer was extracted with CHCl$_3$ (2×500 mL). The combined organic phases were dried over Na$_2$SO$_4$ and concentrated in vacuo to give the product as a red oil. The crude was used in the next step without any further purification.

To a solution of RD 223 (160 mmol) in CH$_3$CN (1 L) was added activated MnO$_2$ (270 g, 3.1 mol). The reaction mixture was heated at 65° C. for 14 h, then filtered (celite) and the residue washed with AcOEt (2×200 mL). The filtrated was concentrated in vacuo (brown solid). DCM (60 mL) was added and the white solid was filtered off. The filtrate was concentrated and purified by FC (Hex:AcOEt 75:25) to give 17.75 g of RD 224 (yield over the two steps 54%) as a yellow solid. Rf=0.52 (Hex/AcOEt 7:3)

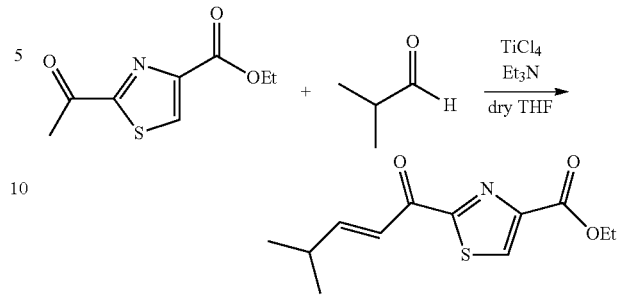

To a solution of RD 224 (4.09 g, 20.6 mmol) in dry THF (50 mL), cooled at 0° C. and under a nitrogen atmosphere, a 1N solution of TiCl$_4$ in toluene (45.3 mL, 45.3 mmol) was added. The solution was stirred for 15 min at 0° C. and, after cooling at −70° C., neat Et$_3$N (6.3 mL, 45.3 mmol) was added. The resulting mixture was stirred for 10 min at −70° C., then neat isobutyr-aldheyde (2.44 mL, 26.8 mmol) was added dropwise. The reaction was stirred for 1 h at −70° C., then allowed to warm to rt. The reaction was quenched with a saturated aqueous solution of NH$_4$Cl (50 mL). The layers were separated and the aqueous phase was extracted with AcOEt (1×50 mL). The collected organic phases were dried over anhydrous Na$_2$SO$_4$, filtered and the solvent was removed in vacuo. The residue was purified by FC (n-Hex/AcOEt 9:1), affording 2.75 g of MSRD 225 (52% yield) as colorless oil. Rf=0.5 (Hex/AcOEt 8:2)

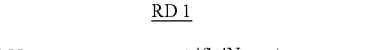

To a solution of NaN$_3$ (5.34 g, 82.35 mmol) in a mixture of H$_2$O (13.5 mL)/DCM (22.5 mL), cooled at 0° C., Tf$_2$O (2.79 mL, 16.65 mmol) was added over a period of 5 min, while the stirring was continued for 2 h. The mixture was placed in a separatory funnel and the organic phase was removed. The aqueous layer was extracted with DCM (2×10 mL). The collected organic phases, containing the triflyl azide, were washed once with a saturated aqueous solution of NaHCO$_3$ and used without further purification. Ile (1.098 g, 8.37 mmol) was combined with K$_2$CO$_3$ (1.732 g, 12.57 mmol), CuSO$_4$ 5H$_2$O (21 mg, 83.7 µmol), distilled H$_2$O (27 mL) and MeOH (54 mL). The triflyl azide in DCM was added and the mixture was stirred overnight. The organic solvents were removed in vacuo and the aqueous phase was diluted with H$_2$O (100 mL). This aqueous mixture was acidified to pH 6 with concentrated HCl and diluted with 0.25 M pH 6.2 phosphate buffer (100 mL) and extracted with AcOEt (4×100 mL) to remove the sulphonamide by-product. The aqueous phase was acidified until pH 2 with concentrated HCl. The product was obtained by extraction with AcOEt (3×100 mL). The organic extracts were combined, dried over anhydrous Na$_2$SO$_4$, filtered and the solvent was removed in vacuo to give 1.170 g of pure RD 1 (yield 89%) as a pale oil.

RD 248

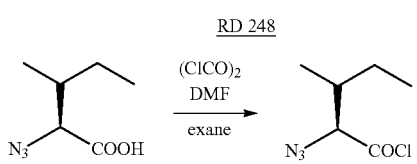

To a solution of azide (2.52 g, 16 mmol) in hexane (250 mL), oxalyl chloride (6.3 mL, 72 mmol) and DMF (1.2 mL, 16 mmol) were added. The reaction mixture was stirred for 1 h and the solvent was removed in vacuo to give pure RD 248 in a quantitative yield.

RD 249

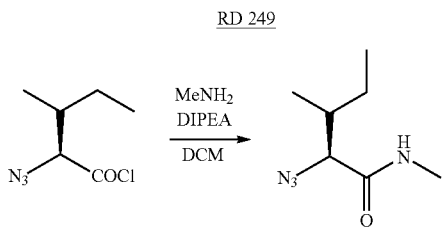

To a solution of MeNH$_2$ (8M solution in EtOH, 10 mL, 80 mmol) and DIPEA (8.2 mL, 48 mmol) in DCM (100 ml), cooled at 0° C., a solution of Ile azide (16 mmol) in DCM (5 mL) was added. The reaction mixture was stirred for 30 min and quenched with H$_2$O (50 mL). The layers were separated and the organic phase was dried over anhydrous Na$_2$SO$_4$ and filtered. The solvent was removed in vacuo and the crude was purified by FC (Hex:AcOEt 6:4) to give 1.951 g of RD 249 (yield 73%) as a yellow oil. Rf=0.27 (Hex/AcOEt 7:3)

RD 251

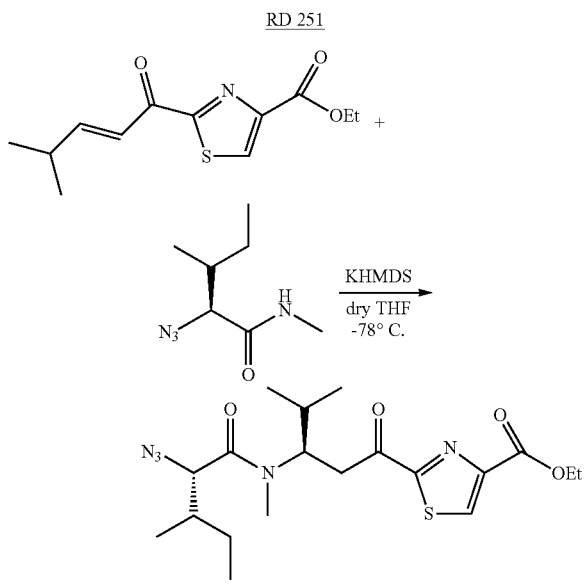

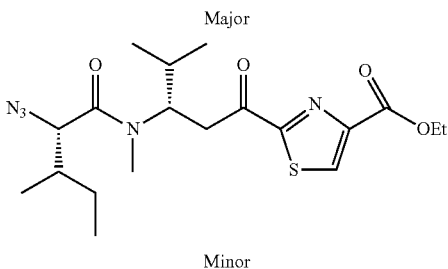

To a solution of azide RD249 (1.752 g, 10.29 mmol) in dry THF (120 mL), cooled at −78° C. and under a nitrogen atmosphere, a solution of KHMDS 0.5 M in toluene (20.6 mL, 10.29 mmol) was added. The reaction mixture became a red gel. After stirring at the same temperature for 5 min, a solution of enone RD225 (1.3 g, 5.14 mmol) in THF (10 mL) was added (purple solution). The reaction mixture was stirred at the same temperature for 1 h and then quenched with a saturated aqueous solution of NH$_4$Cl (100 mL). AcOEt was added (50 mL) and the layers were separated. The organic phase was dried anhydrous Na$_2$SO$_4$, filtered and the solvent was removed in vacuo. The residue was purified by FC (n-Hex/AcOEt 8:2), affording 1.5 g of MSRD 251 (61% yield, the two diastereomers have the same Rf) as colorless oil.

Rf=0.33 (Hex/AcOEt 7:3)

RD 241

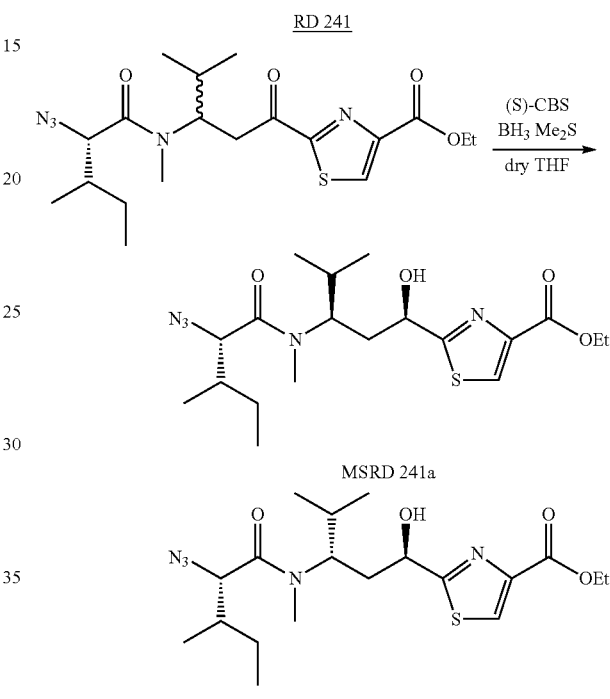

To a 1M solution of commercial (S)-CBS in toluene (290 μL, 0.29 mmol) in dry THF (25 mL) a 10 M solution of BH$_3$ Me$_2$S in THF (266 μL, 2.66 mmol) was added. The solution was stirred for 10 min at r.t. and then cooled at 0° C. A solution of dipeptide (1.152 g, 2.66 mmol) in dry THF (5 mL) was added. The reaction was stirred for 4 h at the same temperature and then quenched with MeOH (2 mL). The solvent was removed in vacuo and the residue was purified by FC (n-Hex/AcOEt 7:3), affording 620 mg of RD 241a and 312 mg of RD 241b (82% overall yield) as a yellow oils. Rf RD 241a=0.26 (Hex/AcOEt 7:3)

RD 199

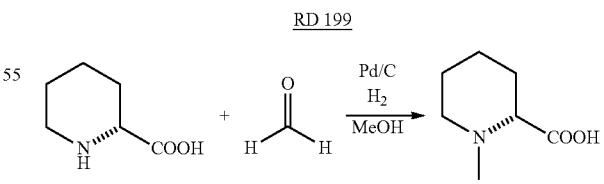

To a suspension of Pipecolinic acid (500 mg, 3.87 mmol) in MeOH (5 mL) were added a 37% aqueous solution of paraformaldehyde (1.16 mL, 15.5 mmol) and a catalytic amount of Pd/C. The reaction mixture was stirred 24 h under a hydrogen atmosphere. The reaction was filtered through Celite and the filtrate was concentrated under reduced pressure to yield 491 mg of MSRD 199 (89% yield) as a white solid.

RD 202

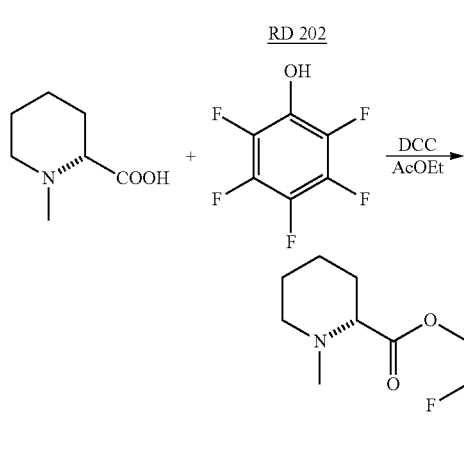

To a suspension of Mep RD199 (70 mg, 0.49 mmol) in AcOEt (2 mL) were added pentafluorophenol (99 mg, 0.54 mmol) and DCC (85 µL, 0.54 mmol). The reaction mixture was stirred for 24 h and filtered (Celite). The activated ester was used immediately without further purification or concentration.

RD 242

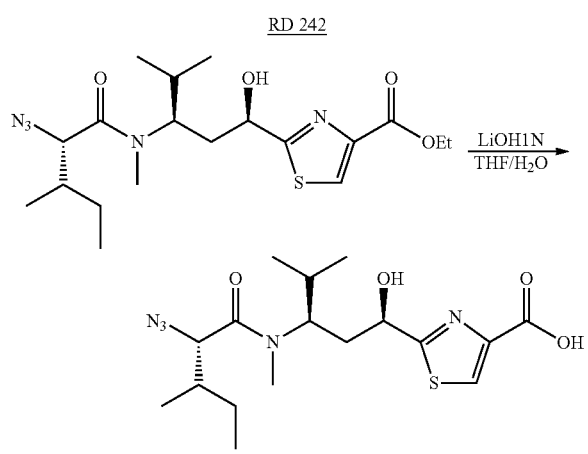

To a solution of RD 241a (459 mg, 1.08 mmol) in a THF/H$_2$O 4:1 mixture (10 mL), LiOH.H$_2$O (68 mg, 1.62 mmol) was added. The reaction was stirred for 5 h, then H$_2$O (10 mL) and AcOEt (20 mL) were added. The layers were separated and a 1 M solution of HCl was added to the aqueous phase until pH 1-2 was reached. The resulting mixture was extracted with AcOEt. The organic phase was dried over anhydrous Na$_2$SO$_4$, filtered and the solvent was removed in vacuo to give 428 mg of pure RD 242 as a white solid.

Rf=0.22 (DCM/MeOH 9:1).

RD 243

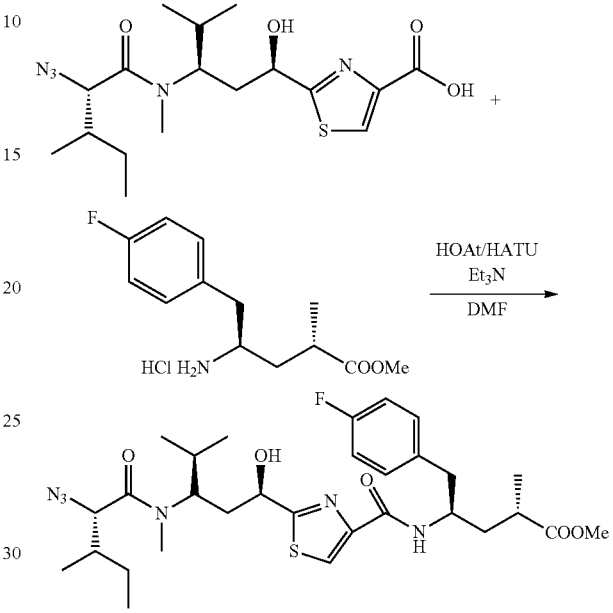

To a solution of RD 242 (349 mg, 0.88 mmol) in DMF (10 mL), HOAt (132 mg, 0.97 mmol), HATU (369 mg, 0.97 mmol) and Et$_3$N (270 µL, 1.9 mmol) were added. After stirring for 5 min a solution of F-Tup RD14 (242 mg, 0.88 mmol) in DMF (1 mL) was added. The reaction mixture was stirred for 1 h. The reaction was diluted with H$_2$O (10 mL) and extracted with Et$_2$O (1×20 mL). The organic phase was washed with a 1N aqueous solution of HCl (1×15 mL), with a saturated aqueous solution of NaHCO$_3$ (1×15 mL) and with brine (2×15 mL). After drying over anhydrous Na$_2$SO$_4$, and filtration, the solvent was removed in vacuo to give 451 mg of pure RD 243 (82% yield) as a white foam.

Rf=0.39 (Hex/AcOEt 1:1)

RD 253

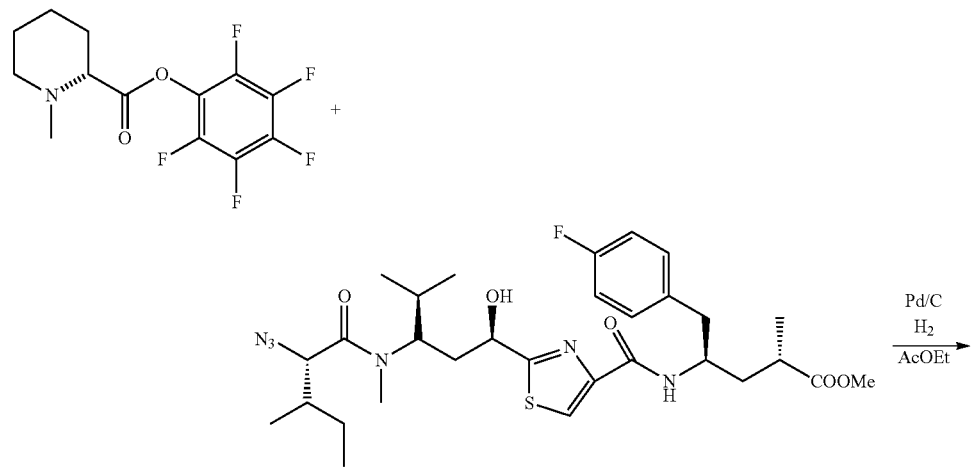

-continued

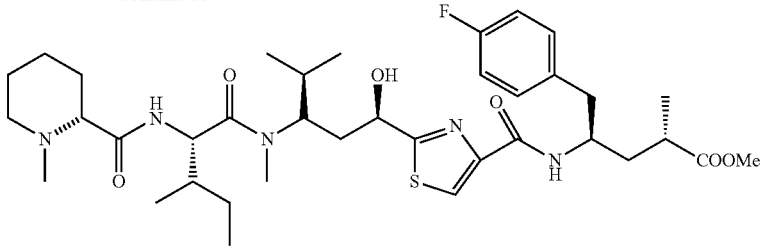

To the solution of crude Mep pentafluorophenylester RD202 (1.05 mmol) were added RD 243 (258 mg, 0.42 mmol) and a catalytic amount of Pd/C. The reaction mixture was stirred 24 h under a hydrogen atmosphere. The reaction was filtered through Celite, and the filtrate was washed with a saturated aqueous solution of NaHCO₃ (1×15 mL). The layers were separated and the organic phase after drying over anhydrous Na₂SO₄ filtered and concentrated under reduced pressure. The crude residue was purified by FC (DCM/AcOEt 1:1, DCM:MeOH 9:1) to give 291 mg of RD 253 (96% yield) as a white solid.
Rf=0.24 (DCM/MeOH 9:1)

was added. The reaction was stirred for 5 days at rt and then acidified with TFA until pH 1-2 was reached. The resulting mixture was washed with H₂O (5 mL) and extracted with AcOEt (10 mL). The organic phase was dried over anhydrous Na₂SO₄, filtered and the solvent was removed in vacuo. The residue was purified by FC (DCM/MeOH 8:2), affording 310 mg of MSRD 257 (quantitative yield) as a white solid.

Rf=0.5 (DCM/MeOHt 8:2).

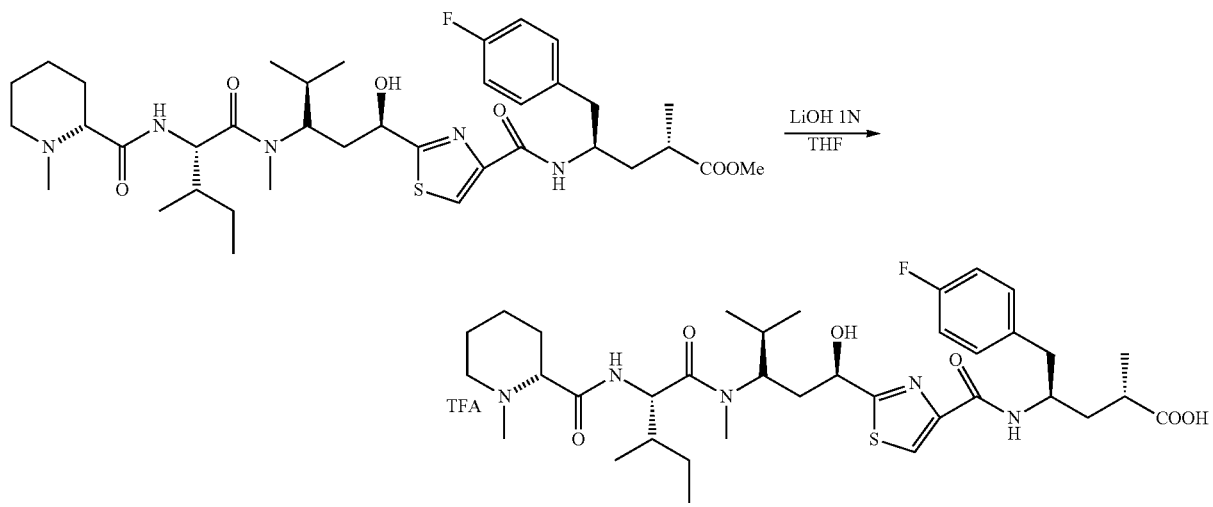

To a solution of RD 253 (290 mg, 0.39 mmol) in THF (5 mL) a 1N aqueous solution of LiOH (1.16 mL, 1.16 mmol)

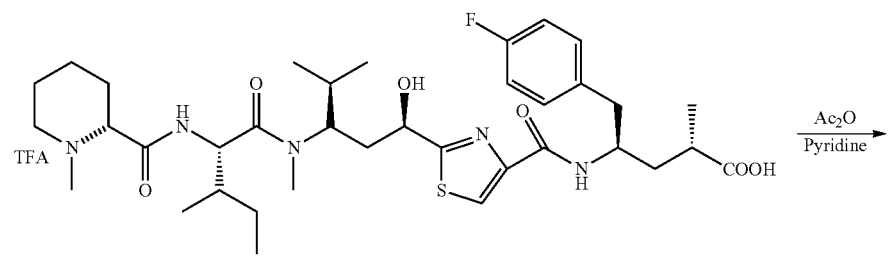

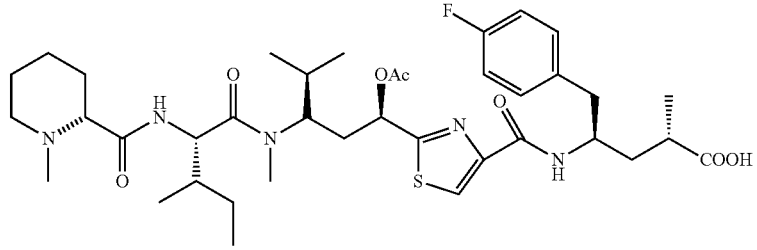

To a solution of RD 257 (310 mg, 0.39 mmol) in pyridine (4 mL), Ac₂O (2 mL) was added and the solution was stirred overnight. The solvents were removed in vacuo. The crude was dissolved with AcOEt (20 mL) and washed with H₂O (2×10 mL). The organic phase was concentrated in vacuo and the crude residue was purified by FC (DCM:MeOH 9:1) to give 240 mg of RD 259 (84% yield) as a white solid. Rf=0.11 (DCM/MeOH 9:1).

Other Building Blocks Used for the Synthesis of the Novel Cytolysine Derivatives:

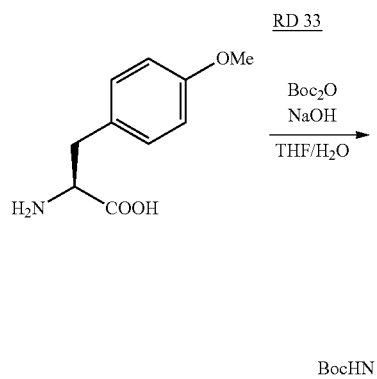

To a solution of p-Methoxy-phenylalanine (1.3 g, 6.6 mmol) and Boc₂O (1.74 g, 7.9 mmol) in a 1:1 mixture of THF/H₂O (30 mL), NaOH (586 mg, 14.6 mmol) was added. The resulting yellow-brown solution was stirred for 5 h and then AcOEt (30 mL) was added. The layers were separated, the aqueous phase was acidified with a 1N aqueous solution of HCl until pH 4 and extracted twice with AcOEt (100 mL). The collected organic phases were dried over Na₂SO₄, filtered and concentrated in vacuo to give 1.8 g (92% yield) of pure RD 33 as a brown oil. Rf=0.37 (CHCl₃/MeOH 9:1)

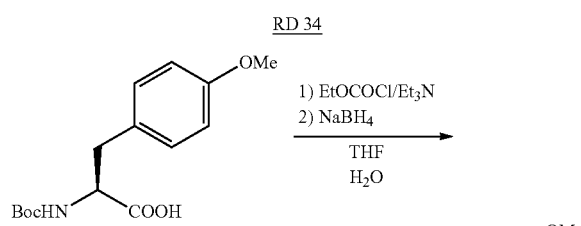

To a solution of RD 33 (1.8 g, 6.1 mmol) in THF (20 mL), cooled at 0° C., ethylchloroformate (700 μL, 7.3 mmol) and Et₃N (1.1 mL, 7.3 mmol) were added. The reaction was stirred at 0° C. for 1 h (white precipitate was formed). The precipitate was filtered off and the filtrate was added to a solution of NaBH₄ (340 mg, 9.15 mmol) in H₂O (10 mL), cooled at 0° C. The temperature was allowed to warm to r.t. and the reaction mixture was stirred for 2 h. The reaction was quenched with a 1N aqueous solution of HCl and extracted with AcOEt (30 mL). After drying over anhydrous Na₂SO₄ and filtration, the solvent was evaporated. The crude was purified by FC (Hex:AcOEt 1:1) to give 1.7 g (99% yield) of RD 34 as white solid.

Rf=0.47 (CHCl₃/MeOH 9:1)

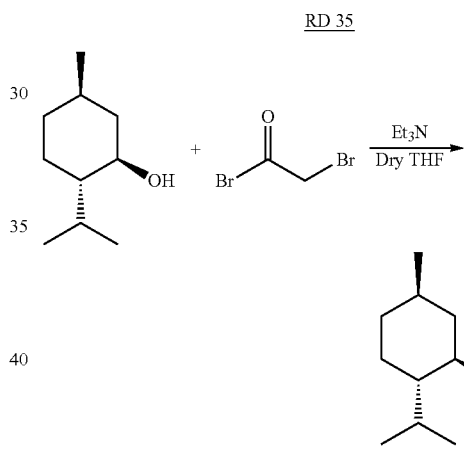

To a solution of menthol (5 g, 32 mmol) in dry THF (30 mL) Et₃N (4.8 mL, 35 mmol) was added. After cooling at 0° C., bromo-acetylbromide (3 mL, 35 mmol) was added dropwise. The temperature was allowed to warm to r.t. and the reaction mixture was stirred for 2 h. After cooling at 0° C., the reaction was quenched with a 1N aqueous solution of HCl (5 mL) and AcOEt was added (30 mL). The layers were separated and the organic phase was dried over Na₂SO₄, filtered and concentrated in vacuo. The crude was purified by FC (Hex:AcOEt 97:3) to give 6.4 g of RD 35 (72% yield) as colorless oil. Rf=0.5 (Hex/AcOEt 98:2)

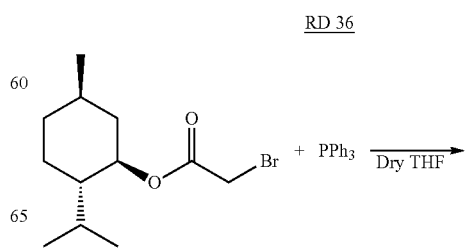

-continued

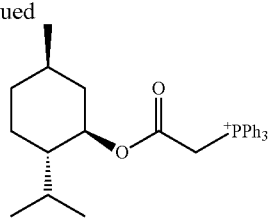

To a solution of RD 35 (6.4 g, 23 mmol) in dry THF (30 mL), under a nitrogen atmosphere, PPh₃ (6 g, 23 mmol) was added. The reaction mixture was refluxed for 2.5 h and concentrated in vacuo. The resulting solid was washed with a 7:3 mixture of hexane/Et₂O and filtered to give 11 g of RD 36 (quantitative yield) as a white solid. Rf=0.87 (CHCl₃/MeOH 7:3)

RD 37

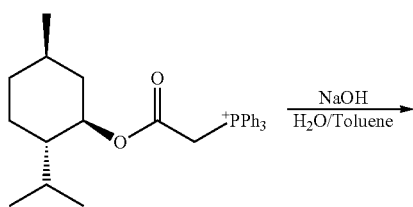

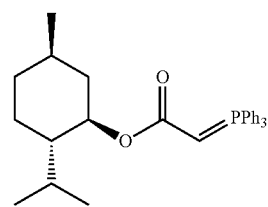

To a suspension of RD 36 (11 g, 23 mmol) in toluene (150 mL) a 0.38 N aqueous solution of NaOH (25 mL) was added dropwise over a period of 5 min. The reaction mixture was stirred for 3 h and the layers were separated. The organic phase was dried over Na₂SO₄, filtered and concentrated in vacuo to give 11 g of RD 37 (quantitative yield) as a white foam.

RD 38

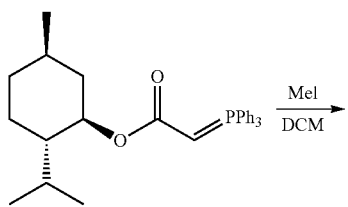

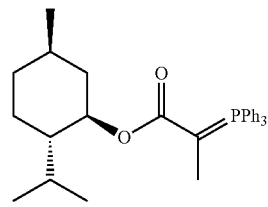

To a solution of RD 37 (11 g, 23 mmol) in DCM (60 mL), cooled at 0° C., MeI (2.1 mL, 34 mmol) was added dropwise. After stirring for 10 min the temperature was allowed to warm to r.t. The reaction mixture was stirred overnight and the solvent was evaporated. The crude was dissolved in toluene (100 mL) and a 0.38 N aqueous solution of NaOH was added. The mixture was stirred for 2 h and the layers were separated. The organic phase was dried over Na₂SO₄, filtered and concentrated to give 10.4 g of RD 38 (96% yield) as a yellow oil. Rf=0.6 (CHCl₃/MeOH 8:2).

RD 39

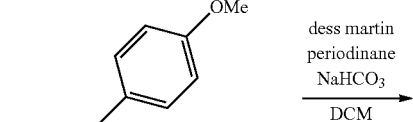

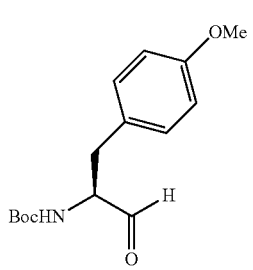

To a solution of RD 34 (1.85 g, 6.4 mmol) in DCM (100 mL) NaHCO₃ (11 g, 127 mmol) and Dess-Martin periodinane (4.5 g, 10.2 mmol) were added. The reaction mixture was stirred for 3 h, diluted with Et₂O (100 mL), stirred for 10 min and poured into a saturated aqueous solution of NaHCO₃/Na₂S₂O₃ (100 mL). The stirring was continued until complete neutralisation of the released acid. The layers were separated and the organic phase was dried over Na₂SO₄, filtered and concentrated in vacuo to give 1.8 g (quantitative yield) of pure RD 39 as a white solid. Rf=0.6(Hex/AcOEt 6:4)

RD 40

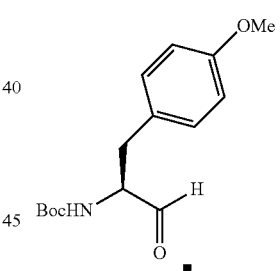

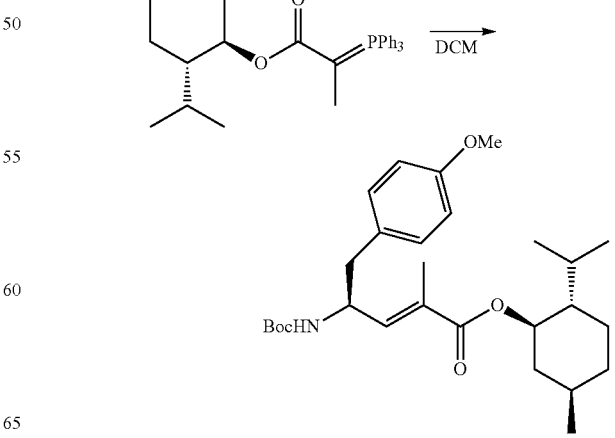

To a solution of menthol ylide (4.53 g, 9.6 mmol) in dry DCM (80 mL), cooled at 0° C., RD 39 (1.8 g, 6.4 mmol) was added. After stirring for 15 min at 0° C., the temperature was allowed to warm to r.t. The reaction mixture was stirred for 8 hours, quenched with a 1N aqueous solution of NaHSO₄ (50 mL) and extracted with DCM (2×50 mL). The organic layer was washed with brine (1×50 mL), dried over Na₂SO₄, filtered and concentrated in vacuo.

The crude was purified by FC (Hex:AcOEt 8:2) to give 2.3 g of FMRD 40 (78% yield) as a white foam. Rf=0.5 (Hex/AcOEt 7:3)

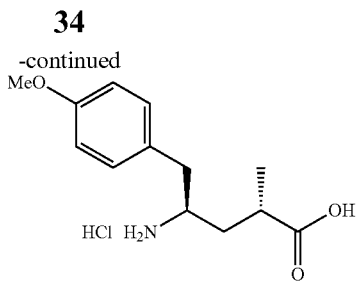

RD 41

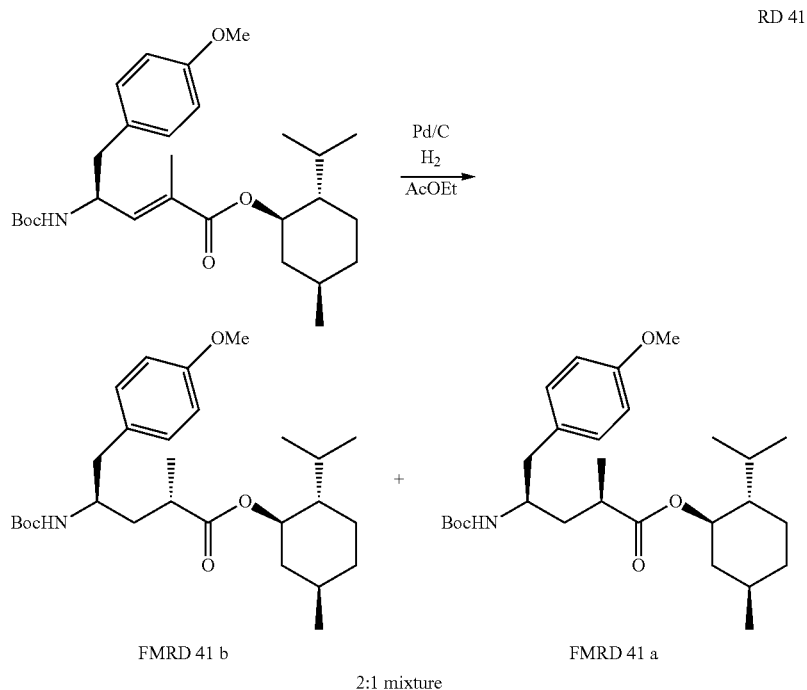

FMRD 41 b             FMRD 41 a

2:1 mixture

To a solution of RD 40 (2.3 mg, 4.85 mmol) in AcOEt (20 mL), a catalytic amount of Pd/C was added. The reaction mixture was stirred under a hydrogen atmosphere overnight and filtered through celite. The filtrate was concentrated under reduced pressure and the crude was purified by FC (Hex/iPrO₂ 55:45) to give 600 mg of FMRD 41a and 1.38 g of RD 41b (85% yield) as white solids. RD 41b Rf=0.32 (Hex/iPrO₂ 55:45)

A suspension of RD 41b (500 mg, 0.42 mmol) in a 6N aqueous solution of HCl (4 mL) was heated at 140° C. for 1.5 h. After cooling at r.t. AcOEt (10 mL) was added and the layers were separated. The aqueous phase was concentrated in vacuo to give 256 mg of pure RD 44 (89% yield). Rf=0.2 (CHCl₃/MeOH 7:3).

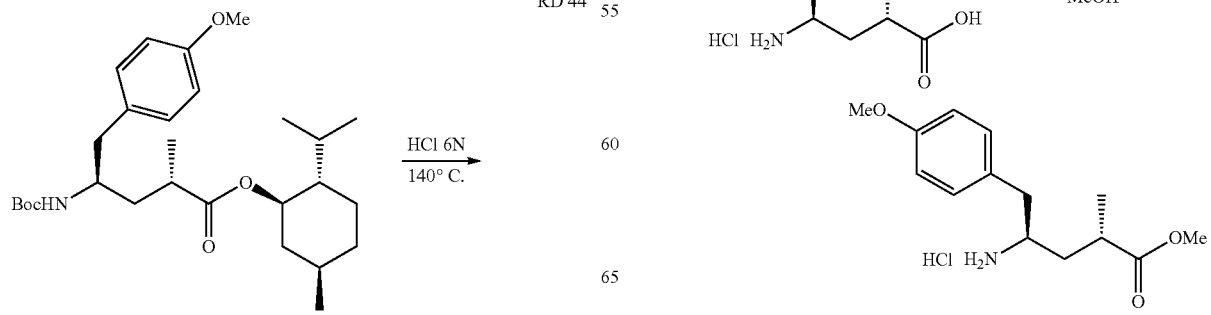

To a solution of RD 44 (150 mg, 0.55 mmol) in MeOH (5 mL) were added 2,2-dimethoxypropane (134 µL, 1.09 mmol) and conc. HCl (1.6 µL, 0.005 mmol). The reaction mixture was heated at 50° C. overnight. The solvent was removed in vacuo to give 125 mg of pure RD 46 (91% yield) as a white solid.

Rf=0.54 (CHCl₃/MeOH 8:2).

Synthesis of N-Me-Tuv Analogue of OMe-Tubulysin D

RD 305

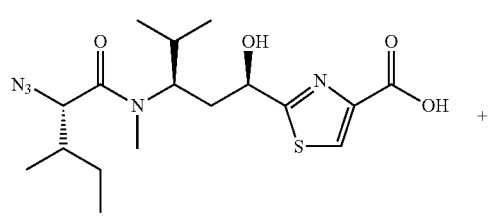

+

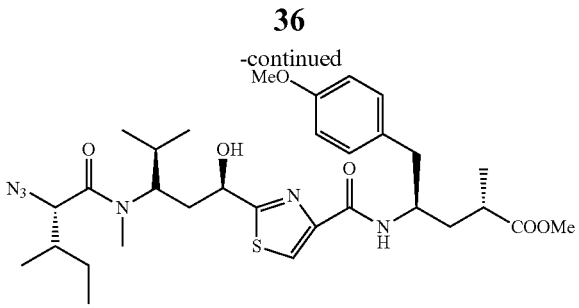

-continued

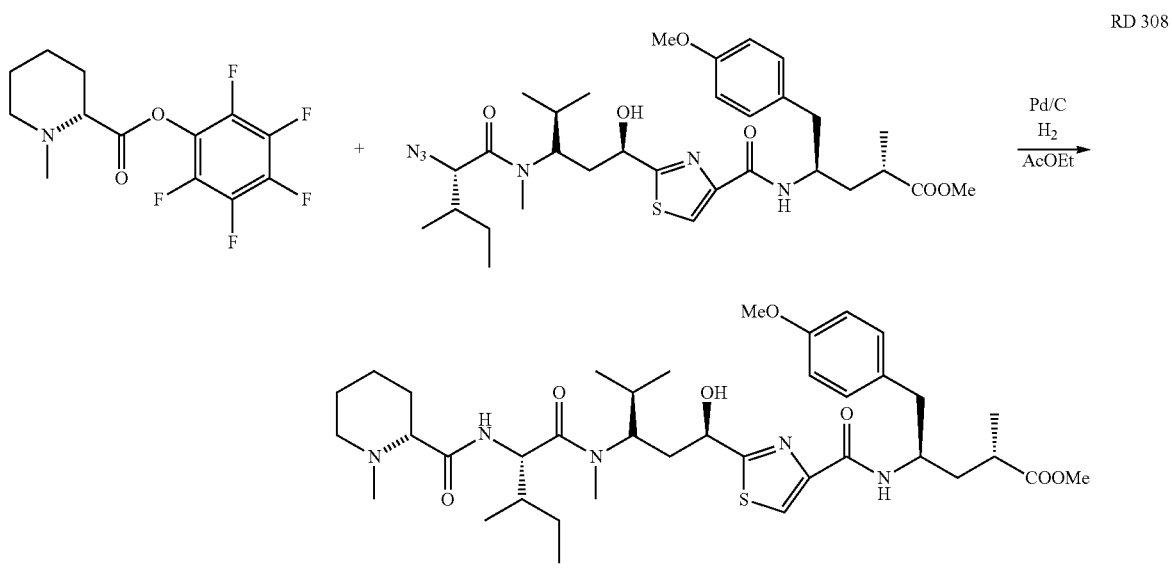

To a solution of acid (178 mg, 0.45 mmol) in DMF (5 mL) HOAt (66 mg, 0.49 mmol), HATU (186 mg, 0.49 mmol) and Et₃N (132 µL, 0.94 mmol) were added. After stirring for 5 min a solution of OMe-Tup (125 mg, 0.45 mmol) in DMF (1 mL) was added. The reaction mixture was stirred for 1 h. The reaction was diluted with H₂O (10 mL) and extracted with Et₂O (1×20 mL). The organic phase was washed with a 1N aqueous solution of HCl (1×15 mL), with a saturated aqueous solution of NaHCO₃ (1×15 mL) and with brine (2×15 mL). After drying over anhydrous Na₂SO₄, and filtration, the solvent was removed in vacuo to give 241 mg of pure RD 305 (85% yield) as a white foam. Rf=0.41 (Hex/AcOEt 4:6).

-continued

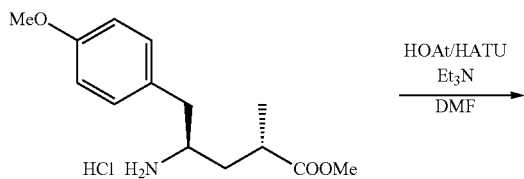

To a solution of crude Mep pentafluorophenylester (0.85 mmol) were added RD 305 (215 mg, 0.34 mmol) and Pd/C. The reaction mixture was stirred 24 h under a hydrogen atmosphere. The reaction was filtered through celite and the filtrate was concentrated under reduced pressure. The crude was dissolved in AcOEt (10 mL) and washed with a saturated aqueous solution of NaHCO₃ (1×15 mL) and with brine (1×15 mL). After drying over anhydrous Na₂SO₄, and filtration, the solvent was removed in vacuo and the crude was purified by FC (Hex/AcOEt 1:1 to elute less polar impurities, DCM:MeOH 9:1 to elute the product) to give 163 mg of RD 308 (66% yield) as a white foam. Rf=0.4 (DCM/MeOH 9:1).

RD 309

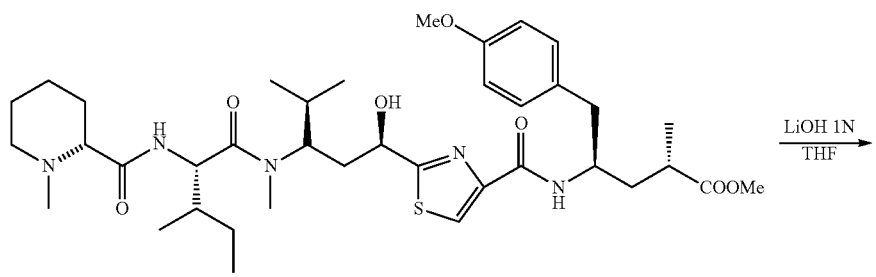

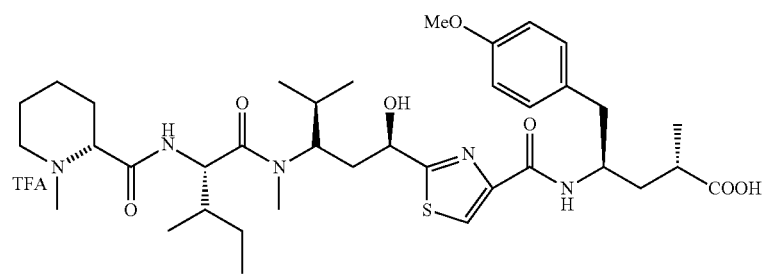

To a solution of RD 308 (153 mg, 0.21 mmol) in THF (5 mL) a 1N aqueous solution of LiOH (630 μL, 0.63 mmol) was added. The reaction was stirred for 5 days and then acidified with TFA until pH 1-2 was reached. The resulting mixture was washed with $H_2O$ (5 mL) and extracted with AcOEt (10 mL). The organic phase was dried over anhydrous $Na_2SO_4$, filtered and the solvent was removed in vacuo. The residue was purified by FC (DCM/MeOH 9:1), affording 173 mg of RD 309 (82% yield) as a white foam.
Rf=0.37 (DCM/MeOH 9:1).

To a solution of RD 309 (153 mg, 0.19 mmol) in pyridine (2 mL) $Ac_2O$ (1 mL) was added and the solution was stirred overnight. The solvent was evaporated, the crude was dissolved in AcOEt (10 mL) and washed with $H_2O$ (10 mL). The layers were separated and the organic phase was washed with brine (1×10 mL). The solvent was removed in vacuo and the crude was purified by FC (DCM:MeOH 9:1) to give 86 mg of RD 311 (60% yield) as a white foam. Rf=0.39 (DCM/MeOH 9:1)

RD 311

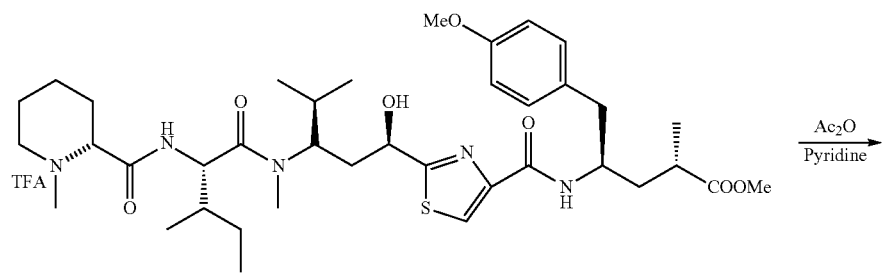

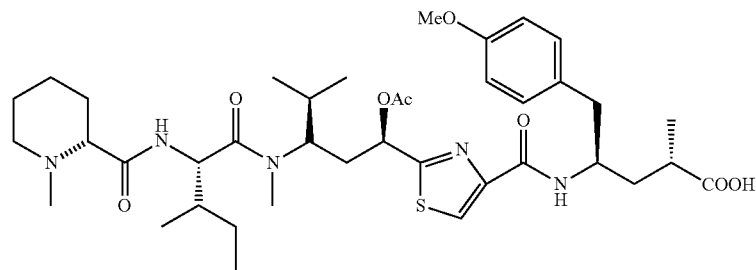

Synthesis of N-Pr-Tuv analogue of F-Tubulysin D
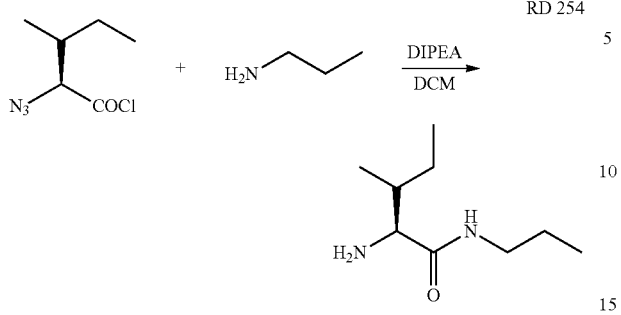
RD 254

To a solution of Propyl amine (3.1 mL, 38 mmol) and DIPEA (3.9 mL, 22.8 mmol) in DCM (50 ml), cooled at 0° C., a solution of Ile azide (7.6 mmol) in DCM (5 mL) was added. The reaction mixture was stirred for 30 min and quenched with $H_2O$ (50 mL). The layers were separated, the organic phase was dried over anhydrous $Na_2SO_4$ and filtered. The solvent was removed in vacuo and the crude was purified by FC (Hex:AcOEt 7:3) to give 1.258 g of RD 254 (yield 83%) as a yellow oil. Rf=0.5 (Hex/AcOEt 7:3)

RD 264

Major

Minor

To a solution of azide (809 mg, 4.08 mmol) in dry THF (30 mL), cooled at −78° C. and under a nitrogen atmosphere, KHMDS 0.5 M in toluene (8.16 mL, 4.08 mmol) was added. After stirring at the same temperature for 5 min, a solution of enone (430 mg, 1.70 mmol) in THF (5 mL) was added (purple solution). The reaction mixture was stirred at the same temperature for 1 h and then quenched with a saturated aqueous solution of $NH_4Cl$ (50 mL). AcOEt was added (50 mL) and the layers were separated. The organic phase was dried over anhydrous $Na_2SO_4$, filtered and the solvent was removed in vacuo. The residue was purified by FC (Hex/AcOEt 8:2), affording 907 g of a 2:1 mixture of azide and MSRD 264 (67% yield, the two diastereomers and the azide have the same Rf) as yellow oil. Rf=0.5 (Hex/AcOEt 7:3).

RD 265

MSRD 265a

MSRD 265b

To a 1M solution of (S)-CBS in toluene (120 µL, 0.12 mmol) in dry THF (5 mL) a 10 M solution of $BH_3$ $Me_2S$ in THF (114 µL, 1.14 mmol) was added. The solution was stirred for 10 min at r.t. and then cooled at 0° C. A solution of dipeptide (515 g, 1.14 mmol) in dry THF (5 mL) was added. The reaction was stirred for 6 h at the same temperature and then quenched with MeOH (2 mL). The solvent was removed in vacuo and the residue was purified by FC (Hex/AcOEt 8:2), affording 275 mg of MSRD 265a and 130 mg of RD 265b (78% overall yield) as yellow oils.

Rf RD 265a=0.39 (Hex/AcOEt 7:3)

Rf RD 265b=0.25 (Hex/AcOEt 7:3)

RD 267

To a solution of RD 265a (224 mg, 0.49 mmol) in a THF/$H_2O$ 4:1 mixture (10 mL), LiOH.$H_2O$ (31 mg, 0.74 mmol)

was added. The reaction was stirred for 5 h, then H₂O (10 mL) and AcOEt (20 mL) were added. The layers were separated and a 1 M aqueous solution of HCl was added to the aqueous phase until pH 1-2 was reached. The resulting mixture was extracted with AcOEt. The organic phase was dried over anhydrous Na₂SO₄, filtered and the solvent was removed in vacuo to give 171 mg of pure RD 267 (82% yield) as a white solid. Rf MSRD 267=0.25 (DCM/MeOH 9:1).

RD 271

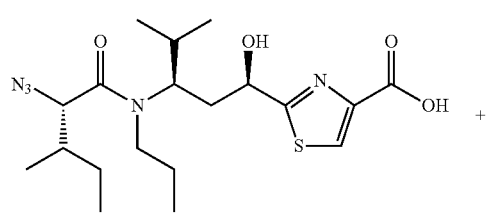

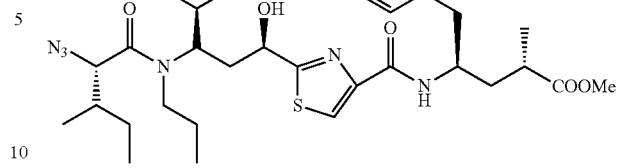

To a solution of RD 267 (157 mg, 0.37 mmol) in DMF (5 mL) HOAt (56 mg, 0.41 mmol), HATU (156 mg, 0.41 mmol) and Et₃N (113 μL, 0.81 mmol) were added. After stirring for 5 min a solution of F-Tup (102 mg, 0.37 mmol) in DMF (1 mL) was added. The reaction mixture was stirred for 1 h. The reaction was diluted with H₂O (10 mL) and extracted with Et₂O (1×20 mL). The organic phase was washed with a 1N aqueous solution of HCl (1×15 mL), with a saturated aqueous solution of NaHCO₃ (1×15 mL) and with brine (2×15 mL). After drying over anhydrous Na₂SO₄, and filtration, the solvent was removed in vacuo to give 173 mg of pure RD 271 (72% yield) as a white foam. Rf=0.54 (Hex/AcOEt 4:6)

RD 273

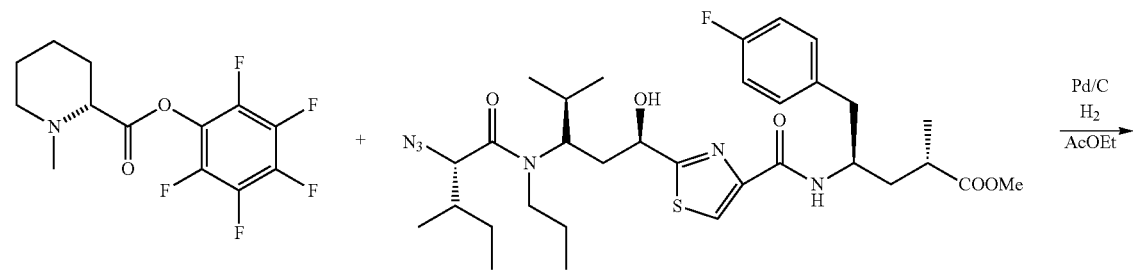

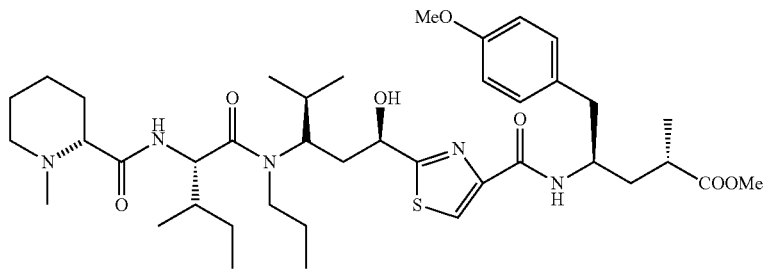

-continued

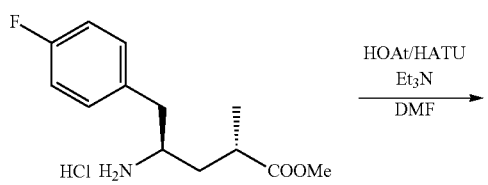

To a solution of crude Mep pentafluorophenylester (0.50 mmol) RD 271 (158 mg, 0.24 mmol) and a catalytic amount of Pd/C were added. The reaction mixture was stirred 24 h under a hydrogen atmosphere. The reaction was filtered through celite and the filtrate was concentrated under reduced pressure. The crude was dissolved in AcOEt (10 mL) and washed with a saturated aqueous solution of NaHCO₃ (1×15 mL) and with brine (1×15 mL). After drying over anhydrous Na₂SO₄, and filtration, the solvent was removed in vacuo and the crude was purified by FC (Hex/AcOEt 1:1 to elute less polar impurities, DCM:MeOH 9:1 to elute the product) to give 107 mg of RD 273 (60% yield) as a white foam. Rf=0.4 (DCM/MeOH 9:1).

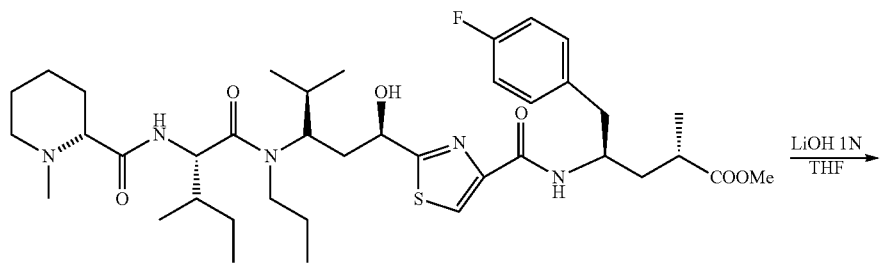

RD 276

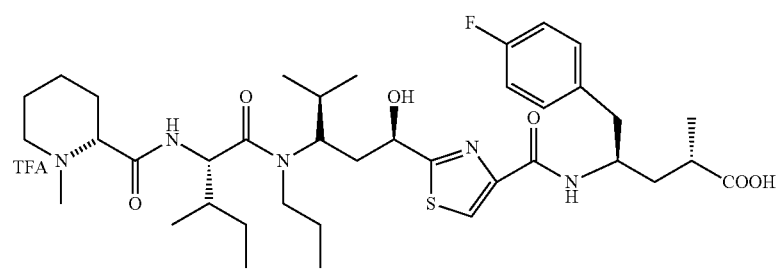

To a solution of RD 273 (90 mg, 0.12 mmol) in THF (5 mL) a 1N aqueous solution of LiOH (420 µL, 0.42 mmol) was added. The reaction was stirred for 5 days and then acidified with TFA until pH 1-2 was reached. The resulting mixture was washed with H₂O (5 mL) and extracted with AcOEt (10 mL). The organic phase was dried over anhydrous Na₂SO₄, filtered and the solvent was removed in vacuo. The residue was purified by FC (DCM/MeOH 9:1), affording 90 mg of MSRD 276 (90% yield) as a white foam.

Rf=0.39 (DCM/MeOH 9:1).

To a solution of RD 276 (85 mg, 0.1 mmol) in pyridine (2 mL) Ac₂O (1 mL) was added and the solution was stirred overnight. The solvent was evaporated, the crude was dissolved in AcOEt (10 mL) and washed with H₂O (10 mL). The layers were separated and the organic phase was washed with brine (1×10 mL). The solvent was removed in vacuo and the crude was purified by FC (DCM:MeOH 9:1) to give 32 mg of RD 282 (41% yield) as a white foam. Rf=0.41 (DCM/MeOH 9:1).

RD 282

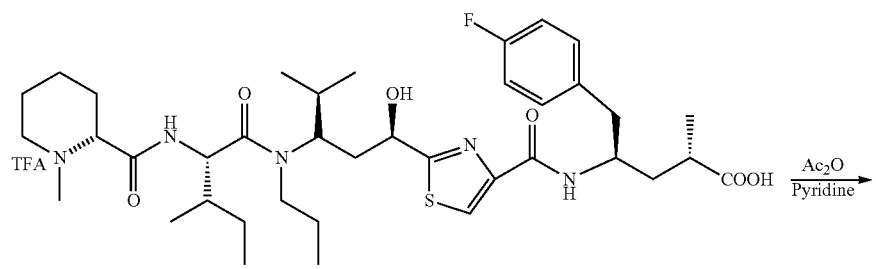

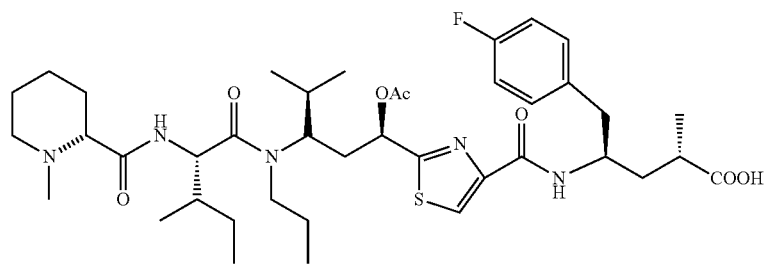

Synthesis of N-Me-Tuv Analogue of Pro-F-Tubulysin D
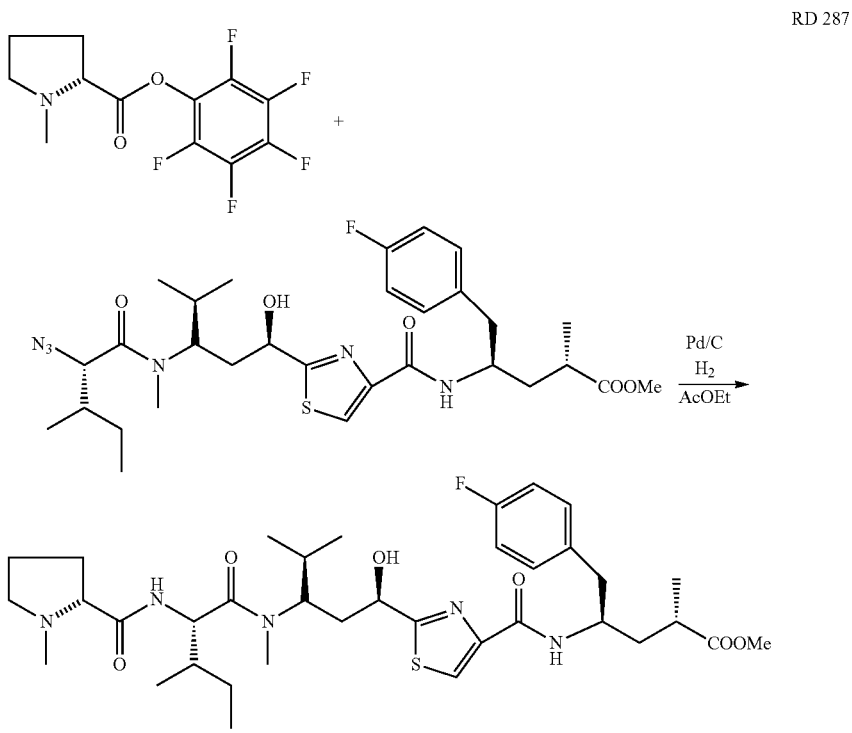
RD 287

To a solution of crude N-Me Pro pentafluorophenylester (0.78 mmol) RD 285 (195 mg, 0.31 mmol) and a catalytic amount of Pd/C were added. The reaction mixture was stirred 24 h under a hydrogen atmosphere. The reaction was filtered through celite and the filtrate was concentrated under reduced pressure. The crude was dissolved in AcOEt (10 mL) and washed with a saturated aqueous solution of $NaHCO_3$ (1×15 mL) and with brine (1×15 mL). After drying over anhydrous $Na_2SO_4$, and filtration, the solvent was removed in vacuo and the crude was purified by FC (Hex/AcOEt 1:1 to elute less polar impurities, DCM:MeOH 9:1 to elute the product) to give 160 mg of RD 287 (73% yield) as a white foam.

Rf=0.6 (DCM/MeOH 9:1)

RD 290

To a solution of RD 287 (150 mg, 0.21 mmol) in THF (5 mL) a 1N aqueous solution of LiOH (640 IL, 0.64 mmol) was added. The reaction was stirred for 18 h and then acidified with TFA until pH 1-2 was reached. The resulting mixture was washed with H₂O (5 mL) and extracted with AcOEt (10 mL). The organic phase was dried over anhydrous Na₂SO₄, filtered and the solvent was removed in vacuo. The residue was purified by FC (DCM/MeOH 9:1), affording 138 mg of RD 290 (82% yield) as a white foam. Rf=0.42 (DCM/MeOH 9:1).

filtrate was added to a solution of NaBH₄ (125 mg, 3.3 mmol) in H₂O (5 mL), cooled at 0° C. The temperature was allowed to warm to r.t. and the reaction mixture was stirred for 2 h. The reaction was quenched with a 1N aqueous solution of HCl and extracted with AcOEt (30 mL). After drying over anhydrous Na₂SO₄ and filtration, the solvent was evaporated. The crude

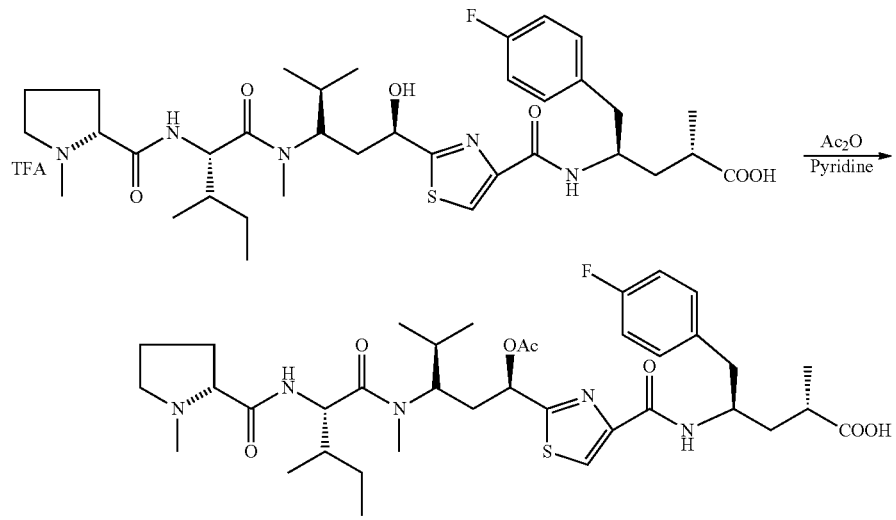

To a solution of RD 290 (120 mg, 0.14 mmol) in pyridine (2 mL) Ac₂O (1 mL) was added and the solution was stirred overnight. The solvent was evaporated, the crude was dissolved in AcOEt (10 mL) and washed with H₂O (10 mL). The layers were separated and the organic phase was washed with brine (1×10 mL). The solvent was removed in vacuo and the crude was purified by FC (DCM:MeOH 9:1) to give 78 mg of RD 291 (76% yield) as a white foam. Rf=0.37 (DCM/MeOH 92:8)

Synthesis of N-Me-Tuv Analogue of p-Phe-Tubulysin D was purified by FC (Hex:AcOEt 1:1) to give 720 mg (quantitative yield) of RD 300 as a white solid. Rf=0.23 (Hex/AcOEt 6:4)

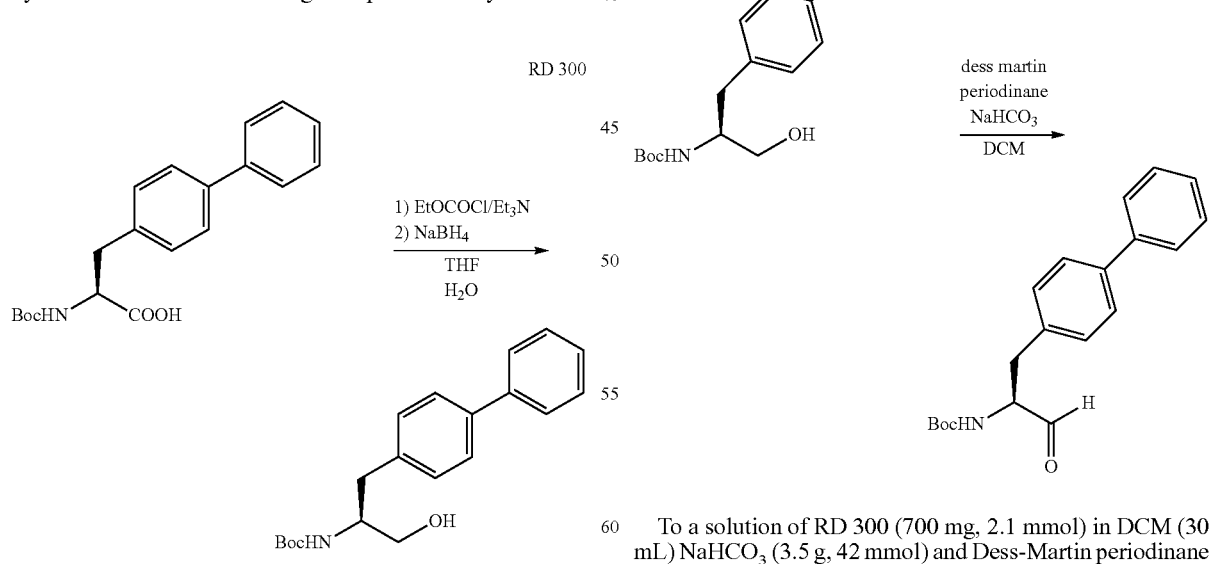

To a solution of Boc protected aminoacid (770 mg, 2.2 mmol) in THF (20 mL), cooled at 0° C., ethylchloroformate (252 µL, 2.64 mmol) and Et₃N (368 µL, 2.64 mmol) were added. The reaction was stirred at 0° C. for 1 h (white precipitate was formed). The precipitate was filtered off and the To a solution of RD 300 (700 mg, 2.1 mmol) in DCM (30 mL) NaHCO₃ (3.5 g, 42 mmol) and Dess-Martin periodinane (1.4 g, 3.4 mmol) were added. The reaction mixture was stirred for 3 h, diluted with Et₂O (50 mL), stirred for 10 min and poured into a saturated aqueous solution of NaHCO₃/Na₂S₂O₃ (50 mL). The stirring was continued until complete neutralisation of the released acid. The layers were separated and the organic phase was dried over Na₂SO₄, filtered and concentrated in vacuo to give 650 mg (95% yield) of pure MSRD 310 as a white solid. Rf=0.38 (Hex/AcOEt 6:4).

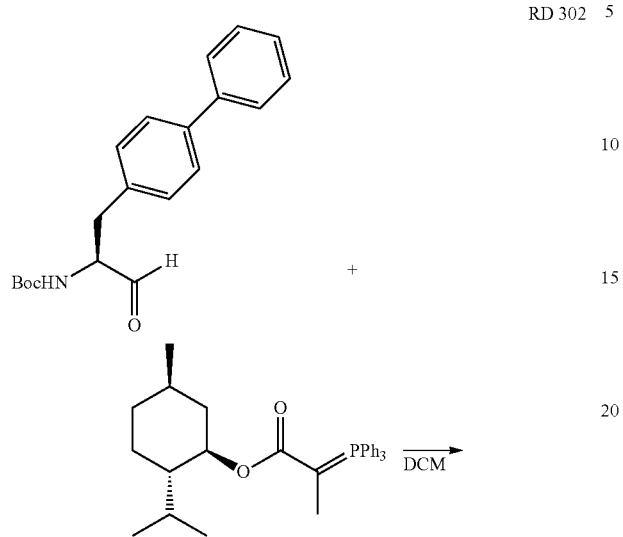

RD 302

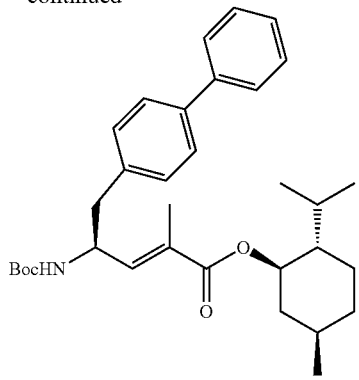

To a solution of menthol ylide (1.4 g, 2.99 mmol) in dry DCM (30 mL), cooled at 0° C., RD 301 (650 mg, 1.99 mmol) was added. After stirring for 15 min at 0° C., the temperature was allowed to warm to r.t. The reaction mixture was stirred for 8 hours, quenched with a 1N aqueous solution of NaHSO$_4$ (50 mL) and extracted with DCM (2×50 mL). The organic layer was washed with brine (1×50 mL), dried over Na$_2$SO$_4$, filtered and concentrated in vacuo. The crude was purified by FC (Hex:AcOEt 8:2) to give 750 mg of RD 302 (72% yield) as a white foam. Rf=0.35 (Hex/iPrO$_2$ 55:45).

RD 304

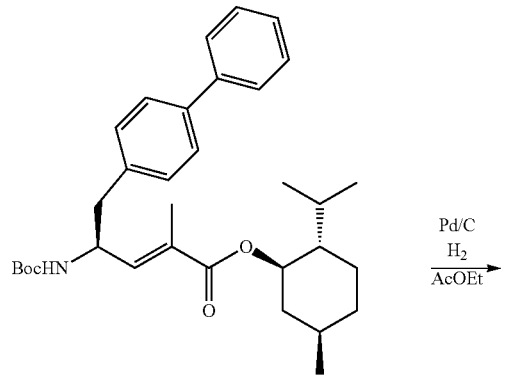

2:1 mixture

To a solution of RD 302 (650 mg, 1.25 mmol) in AcOEt (10 mL), a catalytic amount of Pd/C was added. The reaction mixture was stirred under a hydrogen atmosphere overnight and filtered through celite. The filtrate was concentrated under reduced pressure and the crude was purified by FC (Hex/iPrO$_2$ 6:4) to give 165 mg of RD 304a and 329 mg of RD 304b (75% yield) as white solids. RD 41b Rf=0.32 (Hex/iPrO$_2$ 55:45).

To a solution of RD 44 (150 mg, 0.55 mmol) in MeOH (5 mL) were added 2,2-dimethoxypropane (134 µL, 1.09 mmol) and conc. HCl (1.6 µL, 0.005 mmol). The reaction mixture was heated at 50° C. overnight. The solvent was removed in vacuo to give 125 mg of pure RD 46 (91% yield) as a white solid.

Rf=0.54 (CHCl$_3$/MeOH 8:2).

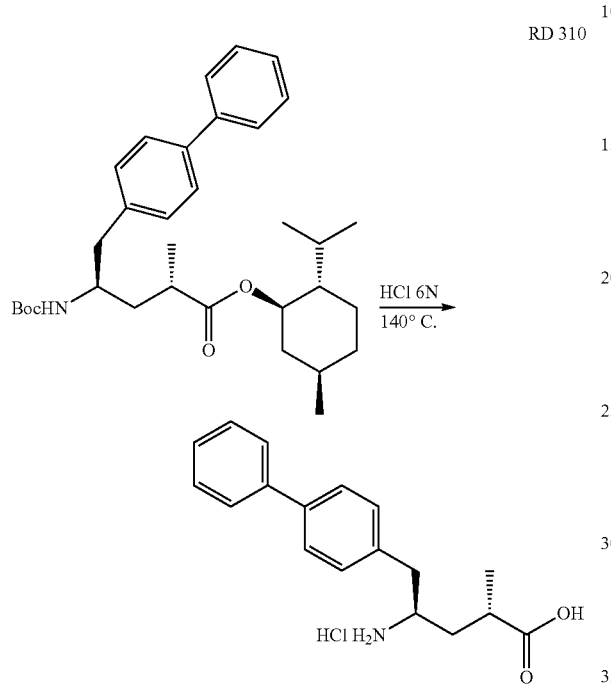

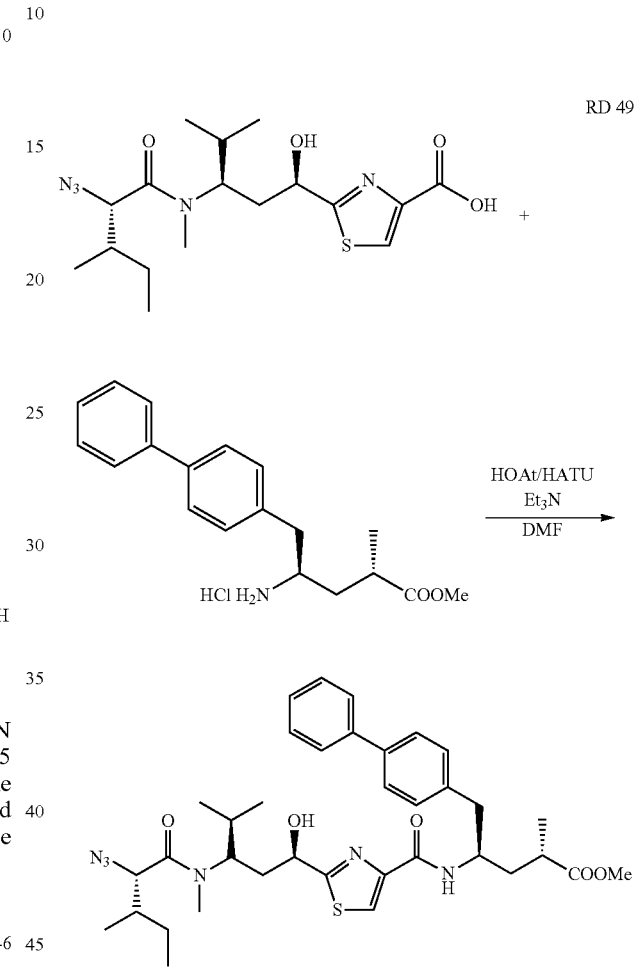

A suspension of RD 304b (319 mg, 0.61 mmol) in a 6N aqueous solution of HCl (4 mL) was heated at 140° C. for 1.5 h. After cooling at r.t. AcOEt (10 mL) was added and the layers were separated. The aqueous phase was concentrated in vacuo to give 150 mg of pure RD 310 (89% yield) as a white solid. Rf=0.3 (CHCl$_3$/MeOH 7:3).

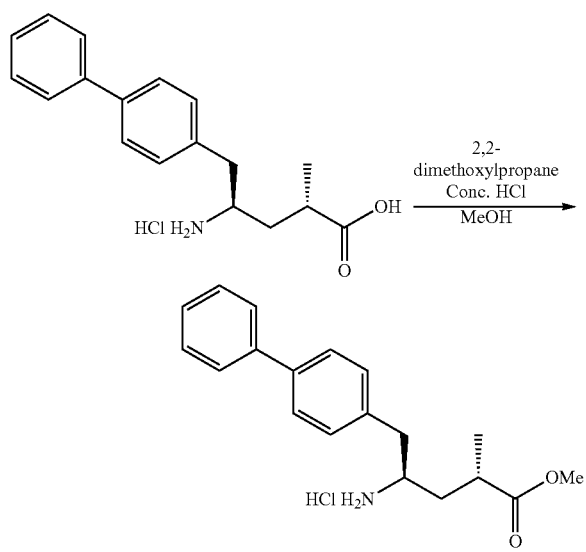

To a solution of acid (117 mg, 0.29 mmol) in DMF (5 mL) HOAt (44 mg, 0.32 mmol), HATU (123 mg, 0.32 mmol) and Et$_3$N (86 µL, 0.62 mmol) were added. After stirring for 5 min a solution of Phe-Tup (98 mg, 0.29 mmol) in DMF (1 mL) was added. The reaction mixture was stirred for 1 h. The reaction was diluted with H$_2$O (10 mL) and extracted with Et$_2$O (1×20 mL). The organic phase was washed with a 1N aqueous solution of HCl (1×15 mL), with a saturated aqueous solution of NaHCO$_3$ (1×15 mL) and with brine (2×15 mL). After drying over anhydrous Na$_2$SO$_4$, and filtration, the solvent was removed in vacuo to give 189 mg of pure RD 49 (96% yield) as a white foam.

Rf=0.29 (Hex/AcOEt 1:1).

RD 51

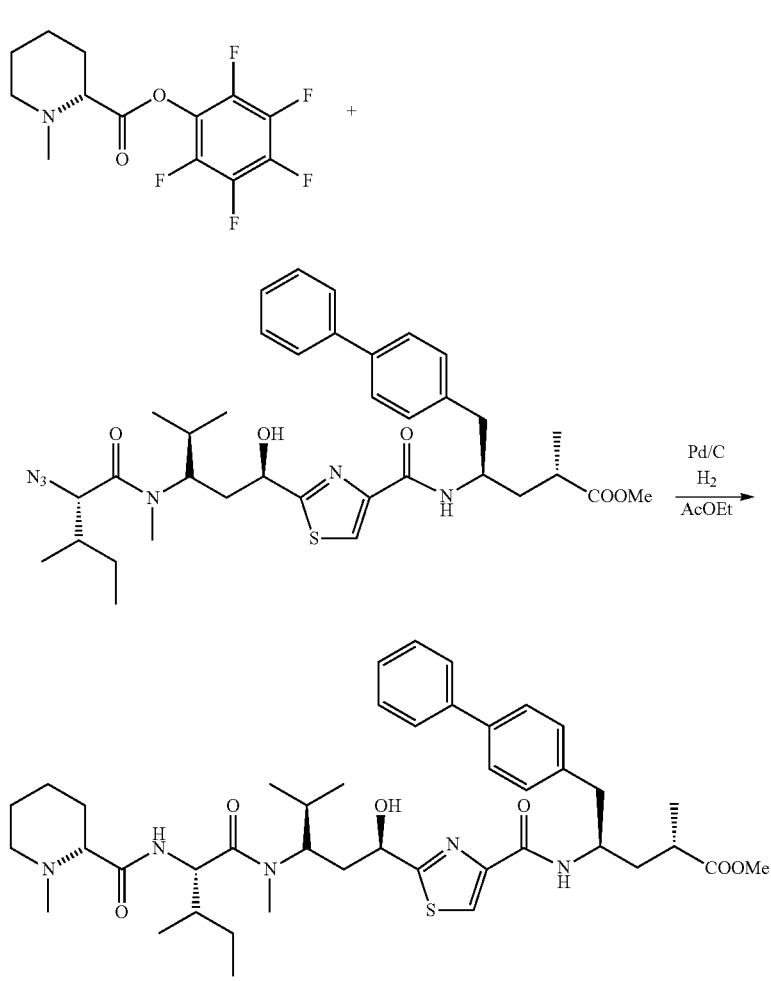

To a solution of crude Mep pentafluorophenylester (0.65 mmol) RD 49 (176 mg, 0.26 mmol) and a catalytic amount of Pd/C were added. The reaction mixture was stirred 24 h under a hydrogen atmosphere. The reaction was filtered through celite and the filtrate was concentrated under reduced pressure. The crude was dissolved in AcOEt (10 mL) and washed with a saturated aqueous solution of $NaHCO_3$ (1×15 mL) and with brine (1×15 mL). After drying over anhydrous $Na_2SO_4$, and filtration, the solvent was removed in vacuo and the crude was purified by FC (Hex/AcOEt 1:1 to elute less polar impurities, DCM:MeOH 9:1 to elute the product) to give 158 mg of RD 51 (78% yield) as a white foam. Rf=0.42 (DCM/MeOHt 9:1).

RD 312

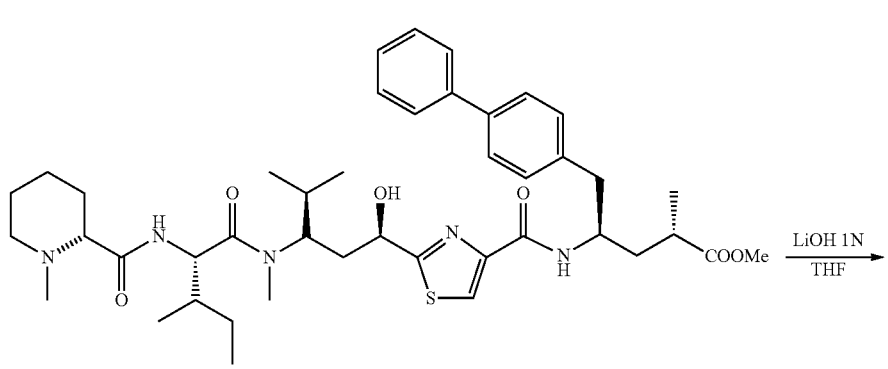

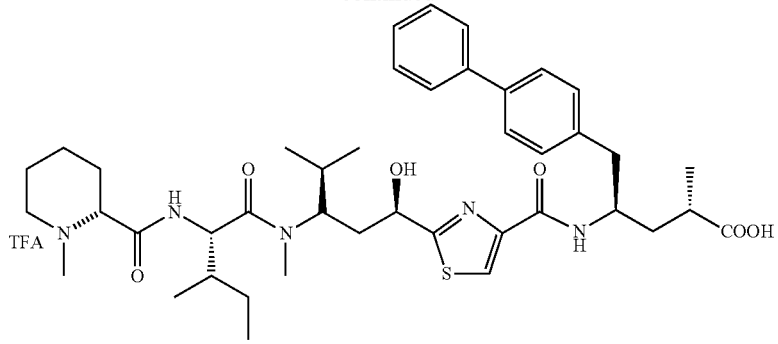

To a solution of RD 51 (148 mg, 0.19 mmol) in THF (5 mL) a 1N aqueous solution of LiOH (57 μL, 0.57 mmol) was added. The reaction was stirred for 5 days and then acidified with TFA until pH 1-2 was reached. The resulting mixture was washed with H₂O (5 mL) and extracted with AcOEt (10 mL). The organic phase was dried over anhydrous Na₂SO₄, filtered and the solvent was removed in vacuo. The residue was purified by FC (DCM/MeOH 9:1), affording 135 mg of MSRD 312 (83% yield) as a white foam. Rf=0.29 (DCM/MeOHt 9:1).

Activity Tests

The activity of some representative example compounds according to the invention has been determined according to the following procedure:

Seed 96-well plates at a concentration of 5000 cells/well in a volume of 100 μl with A2780 (ovarian), HT-29 (colon), MDA-MB-231 (breast), NCI-H1299 (non-small cell lung, MCF-7 (breast) cells or any other available cancer cell line. Incubate for 24 hours at 37° C.

RD 313

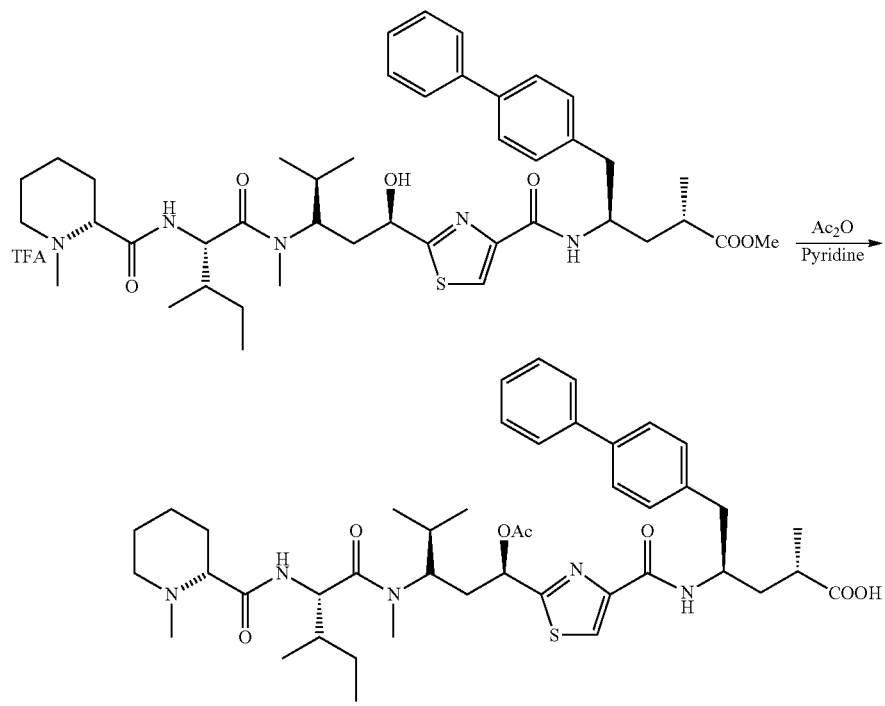

To a solution of RD 312 (125 mg, 0.14 mmol) in pyridine (2 mL) Ac₂O (1 mL) was added and the solution was stirred overnight. The solvent was evaporated, the crude dissolved in AcOEt (10 mL) and washed with H₂O (10 mL). The layers were separated and the organic phase was washed with brine (1×10 mL). The solvent was removed in vacuo and the crude was purified by FC (DCM:MeOH 9:1) to give 70 mg of RD 313 (62% yield) as a white foam.

Rf=0.35 (DCM/MeOHt 9:1).

Prepare a stock solution of Tubulysin derivative by dissolving at 10 mg/ml in methanol. Prepare dilutions of 1 mg/ml in methanol and 17 μg/ml (20 μM) in cell culture medium, and make serial 10-fold dilutions down to 2 pM in cell culture medium.

Add 100 μl of Tubulysin to triplicate wells for a final dose range of 1 pM to 10 μM. Reserve three wells for "untreated" cells and three wells of medium alone as a "blank". Incubate plates at 37° C. for 48 hours.

Prepare MTS assay reagent by diluting CellTiter 96 AQ$_{ueous}$ One Solution (Promega) 5-fold into PBS/glucose (4.5 g/L). Aspirate cell culture medium. Aliquot 100 μl of MTS reagent to each well. Incubate at 37° C. for 1-2 hours depending on the cell line.

Shake the plates for 5 minutes and measure the absorbance at 485 nm using a plate reader (e.g. Tecan). Enter the raw data into an excel spreadsheet to obtain the % cell survival for each cell line. Graph dose (nM) vs. % cell survival and estimate $IC_{50}$s from the graphs.

Use a 4-parameter logistic fit to obtain $IC_{50}$ values:

$$y=(a-d)/(1+(x/c)^b)+d$$

where
x=dose
y=% cell survival
a=lower asymptote
b=slope
c=$IC_{50}$
d=upper asymptote Enter values for x and y. Estimate values for a, b, c, and d. Run the solver tool on the sum of squared errors cell. Minimize the sum of squared errors by varying parameters a through d. Obtain the $IC_{50}$ (nM) from parameter c.

Tubulysin A has been used as reference. The results are shown in Table 1.

TABLE 1

| Compound | IC50 cell line [nM] | | | |
| --- | --- | --- | --- | --- |
| | HT-29 | A2780 | NCI-H1299 | MCF-7 |
| 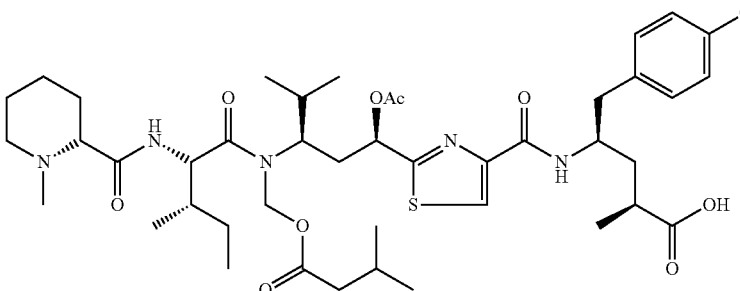 Tubulysin A (Reference) | 0.75 | 0.8 | | 0.6 |
| 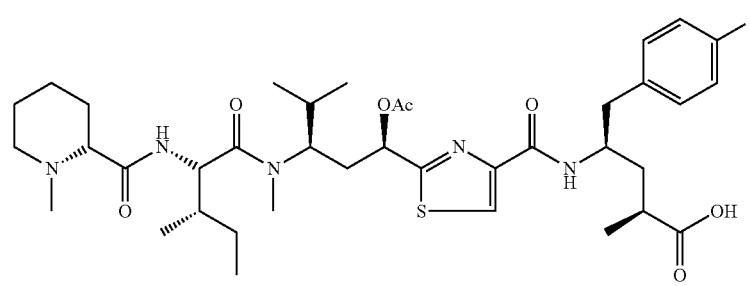 RD259 | 3.0 | 0.8 | 1.93 | |
| 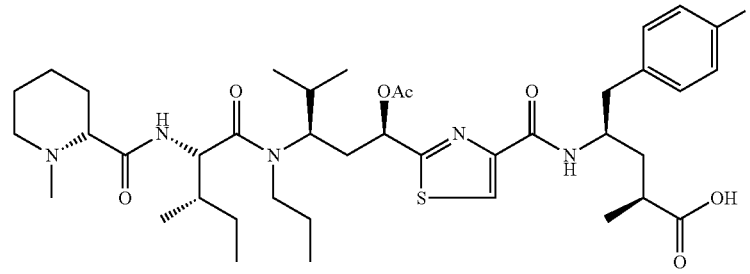 RD282 | 0.48 | 0.30 | 0.52 | 0.4 |

TABLE 1-continued
| Compound | IC50 cell line [nM] | |
|---|---|---|
| 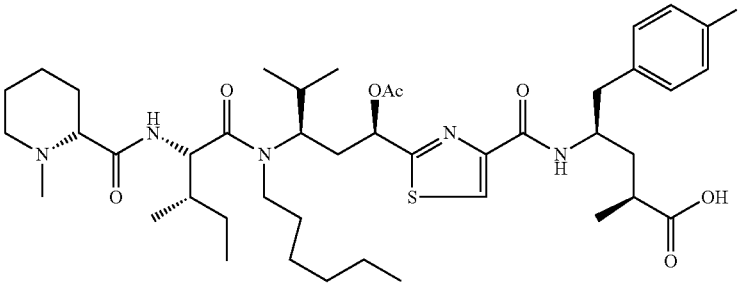RD295 | HT-29 0.43 | |
| 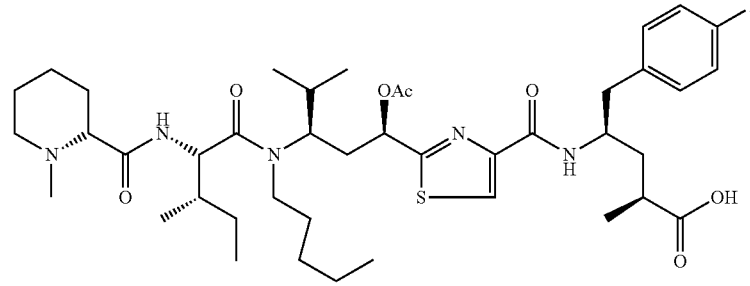RD305 | HT-29 0.35 | MCF-7 0.6 |
| 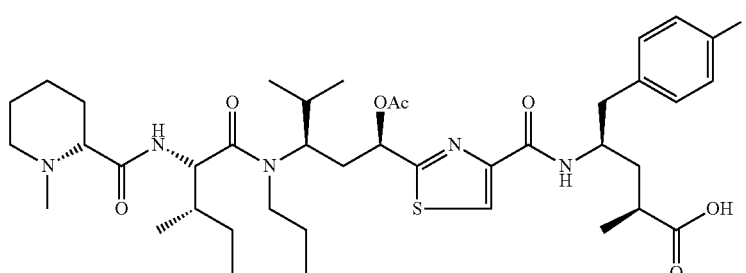RD314 | HT-29 0.28 | MCF-7 0.4 |
| 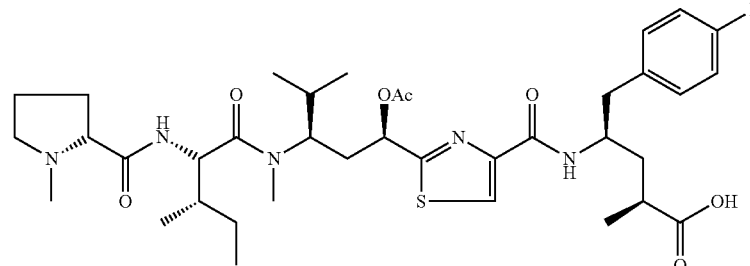RD291 | HT-29 3.1 | MCF-7 1.1 |

TABLE 1-continued
| Compound | IC50 cell line [nM] | | |
|---|---|---|---|
| 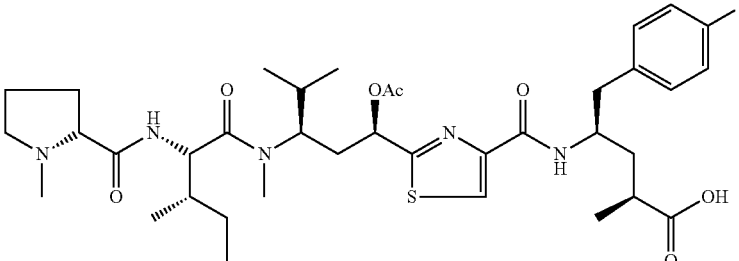 RD307 | HT-29 2.1 | A2780 0.7 | |
| 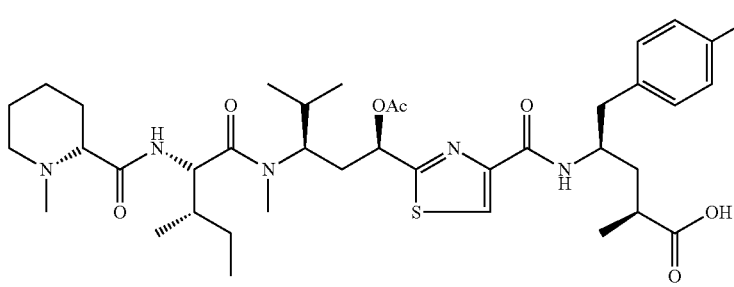 RD311 | HT-29 2.0 | A2780 0.8 | MCF-7 0.6 |
| 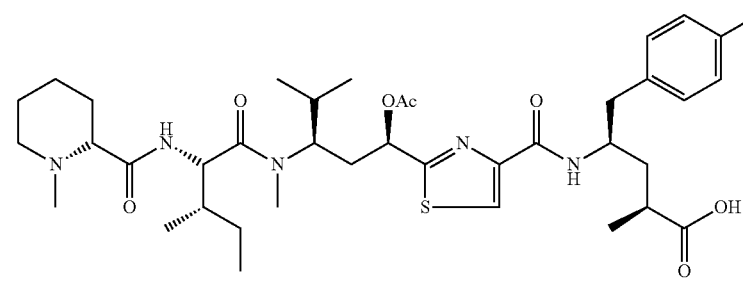 RD313 | HT-29 2.3 | A2780 1.4 | |
| 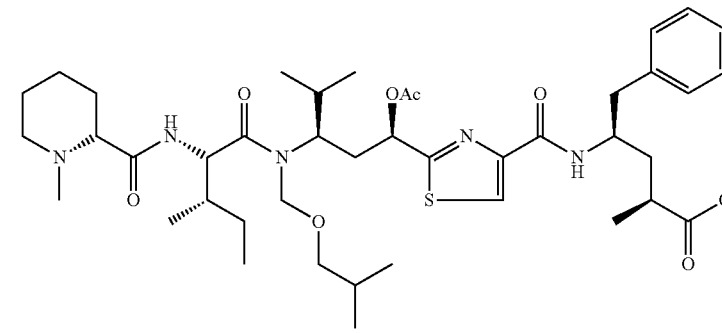 RD321 | HT-29 3.5 | A2780 0.9 | MCF-7 1.1 |

TABLE 1-continued
| Compound | IC50 cell line [nM] | |
|---|---|---|
| 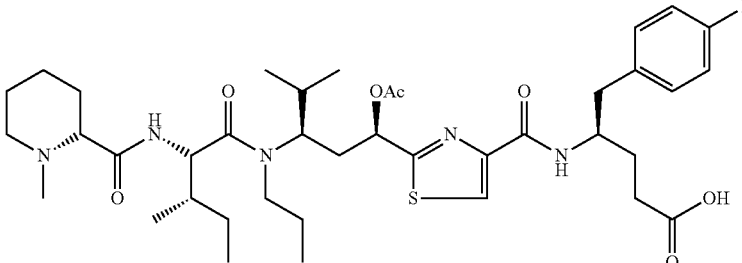 RD330 | HT-29<br>0.49 | A2780<br>0.3 |
| 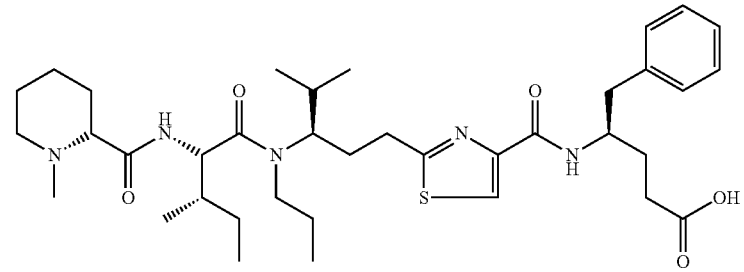 RD339 | HT-29<br>3.1 | A2780<br>1.1 |
| 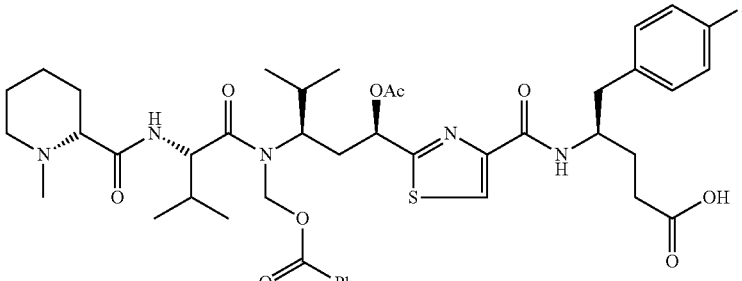 RD341 | HT-29<br>0.45 | MCF-7<br>0.4 |
| 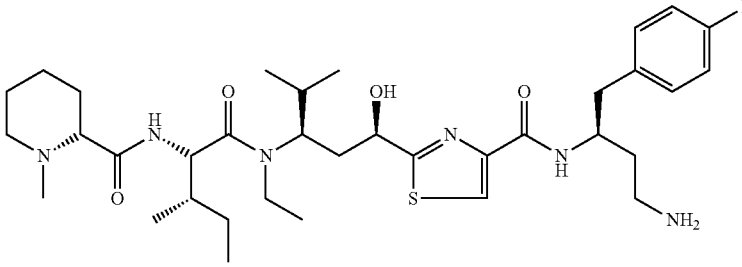 RD344 | HT-29<br>23.0 | MCF-7<br>15.2 |
| 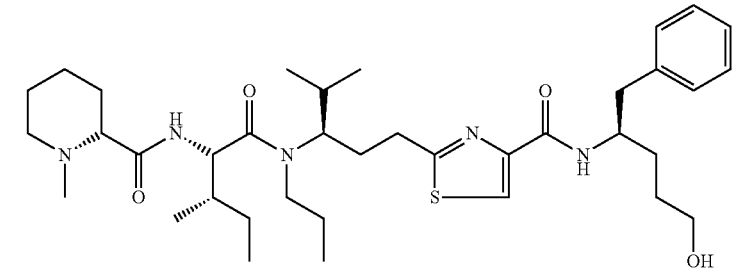 RD353 | HT-29<br>4.3 | A2780<br>1.6 |

In general the new molecules according to this invention show an activity against several cancer cell lines between 0.03 to 60 nM.

The invention claimed is:
1. A compound of Formula (IV),

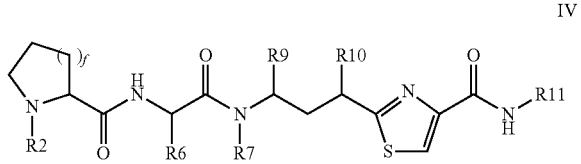

wherein
$R^2$ is $C_1$-$C_4$ alkyl;
$R^6$ is $C_1$-$C_6$ alkyl;
$R^7$ is $C_1$-$C_6$ alkyl, $CH_2$-Phenyl, $CH_2OR^{19}$ or $CH_2OCOR^{20}$, wherein $R^{19}$ is alkyl, $R^{20}$ is phenyl, or $CH_2$-Phenyl;
$R^9$ is $C_1$-$C_6$ alkyl;
$R^{10o}$ is H, OH, O-alkyl or O-acetyl;
f is 1 or 2;
$R^{11}$ is a group of the Formula (II)

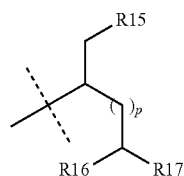

wherein
$R^{15}$ is a group of the formula

wherein $R^{21}$ is H, halogen, OH, $NO_2$, $NH_2$, CN, alkyl, heteroalkyl, cycloalkyl, heterocycloalkyl, aryl, heteroaryl, alkyloxy, alkyl amino or dialkyl amino;
$R^{16}$ is H or $CH_3$;
$R^{17}$ is $CO_2H$, $CO_2R^{18}$, $CONHNH_2$, OH, $NH_2$, SH or an optionally substituted heteroalkyl or heterocycloalkyl group, wherein $R^{18}$ is an optionally substituted alkyl, heteroalkyl or heterocycloalkyl group; and
p is 0, 1, 2 or 3;
or a pharmacologically acceptable salt, a solvate, a hydrate or a pharmacologically acceptable formulation thereof.

2. The compound according to claim 1, wherein $R^2$ is a methyl group.
3. The compound according to claim 1, wherein $R^6$ is an isobutyl group.
4. The compound according to claim 1, wherein p is 1.
5. The compound according to claim 1, wherein $R^{11}$ has the following structure:

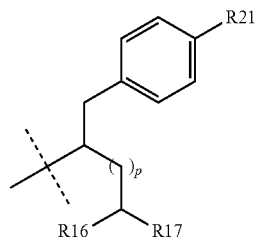

wherein
$R^{21}$ is H, OH, halogen, $NH_2$, alkyloxy, phenyl, alkyl amino or dialkyl amino;
$R^{16}$ is H or $CH_3$;
$R^{17}$ is $CO_2H$, $CO_2R^{18}$, $CONHNH_2$, OH, $NH_2$, SH or an optionally substituted heteroalkyl or heterocycloalkyl group, wherein $R^{18}$ is an optionally substituted alkyl, heteroalkyl or heterocycloalkyl group; and
p is 0, 1, 2 or 3.

6. A pharmaceutical composition comprising a compound according to claim 1 and optionally one or more carriers and/or adjuvants.

7. A method for treating a subject suffering from or susceptible to cancer selected from the group consisting of ovarian, colon, breast and lung cancer, comprising administering to the subject a compound of claim 1.

8. The method of claim 7 wherein the subject is suffering from cancer.

9. A method for providing surface modifications of a plastic or metal implant, comprising use of a compound of claim 1.

10. The method of claim 9 wherein the plastic or metal implant is treated with the compound.

11. The method of claim 9 wherein the plastic or metal implant comprising the compound is implanted into a subject.

12. A compound of the following formula:

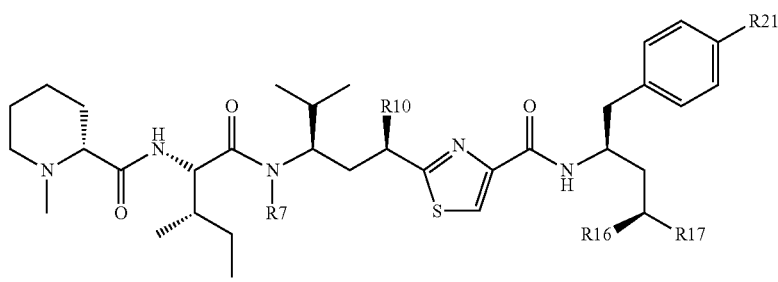

wherein $R^7$ is $C_1$-$C_6$ alkyl, $CH_2Ph$, $CH_2OCH_2CH(CH_3)_2$, $CH_2OCOCH_2Ph$, or $CH_2OCOPh$;

$R^{10}$ is H, O-alkyl, OH or OAc;

$R^{16}$ is $CH_3$ or H;

$R^{17}$ is COOH, $CONHNH_2$, OH, $NH_2$, $CH_2OH$, $CH_2NH_2$ or $CH_2SH$; and $R^{21}$ is H, F, OH, $NH_2$, $CH_3$, OMe or Ph;

or a pharmacologically acceptable salt, a solvate, a hydrate or a pharmacologically acceptable formulation thereof.

13. A pharmaceutical composition comprising a compound according to claim 12 and optionally one or more carriers and/or adjuvants.

14. A method for preparing conjugates comprising at least one compound of Formula (I) or (IV) and a biological molecule, e.g. oligo or poly saccharide, monoclonale antibody, lectine, PSA (prostata specific antigen) or peptidic vector, hormone, vitamin, lipid or a synthetic polymer and optionally also a linker or polymer of natural or unnatural origin, such as a pegylated polymer, starch, cyclodextrine or a mixture of a synthetic polymer with a biological molecule.

* * * * *